(12) United States Patent
Cannell et al.

(10) Patent No.: US 11,222,726 B2
(45) Date of Patent: Jan. 11, 2022

(54) RECEIVER HEALTH SYSTEMS AND METHODS FOR A REAL TIME LOCATION PLATFORM

(71) Applicant: General Electric Company, Schenectady, NY (US)

(72) Inventors: Matthew James Cannell, Glen Allen, VA (US); Philip Crawley, Glen Allen, VA (US); Shawn Reed, Glen Allen, VA (US); Ricardo Alexander, Glen Allen, VA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/474,793

(22) PCT Filed: Dec. 29, 2017

(86) PCT No.: PCT/US2017/069065
§ 371 (c)(1),
(2) Date: Jun. 28, 2019

(87) PCT Pub. No.: WO2018/126199
PCT Pub. Date: Jul. 5, 2018

(65) Prior Publication Data
US 2019/0326015 A1    Oct. 24, 2019

Related U.S. Application Data

(60) Provisional application No. 62/441,201, filed on Dec. 31, 2016.

(51) Int. Cl.
*G06F 3/00* (2006.01)
*G16H 40/67* (2018.01)
(Continued)

(52) U.S. Cl.
CPC ............. *G16H 40/67* (2018.01); *G06F 9/542* (2013.01); *G16H 80/00* (2018.01); *H04L 67/12* (2013.01)

(58) Field of Classification Search
CPC ........................................................ G06F 9/54
(Continued)

(56) References Cited

U.S. PATENT DOCUMENTS 7,404,520 B2 *  7/2008  Vesuna ................... G06K 17/00
                                                           235/462.45
8,682,377 B1 *  3/2014  Khanka ............... H04W 52/346
                                                              455/522

(Continued)

FOREIGN PATENT DOCUMENTS

WO      2013/058985      4/2013

OTHER PUBLICATIONS

Rajeev Bali,The Journal on Information Technology in Healthcare (Year: 2006).*

(Continued)

*Primary Examiner* — Lechi Truong

(57) ABSTRACT

Methods, apparatus, systems and articles of manufacture are disclosed to facilitate proximity detection and location tracking. An example apparatus includes a real time location system (RTLS) health processor. The example RTLS health processor includes an event processor to process an event included in a message from an RTLS device to identify event information related to the RTLS device, the event relating to a health of the RTLS device and the event information including an event type and an event detail. The example RTLS health processor includes a health analyzer to compare the event detail to a prescribed bound for the event type, the event relating to a health of the device. The example RTLS health processor includes an output generator to, (Continued)

when the event detail is outside the prescribed bound, trigger a response to address the event with respect to the RTLS device.

11 Claims, 13 Drawing Sheets

(51) Int. Cl.
*G16H 80/00* (2018.01)
*G06F 9/54* (2006.01)
*H04L 29/08* (2006.01)

(58) Field of Classification Search
USPC .......................................................... 719/310
See application file for complete search history.

(56) References Cited

U.S. PATENT DOCUMENTS

| | | | |
|---|---|---|---|
| 2003/0023146 A1 | 1/2003 | Shusterman | |
| 2008/0130604 A1* | 6/2008 | Boyd | H04W 64/00 |
| | | | 370/338 |
| 2008/0294019 A1 | 11/2008 | Tran | |
| 2009/0227877 A1 | 9/2009 | Tran | |
| 2012/0083258 A1* | 4/2012 | Rabii | H04W 52/0261 |
| | | | 455/418 |
| 2013/0066448 A1* | 3/2013 | Alonso | H04Q 9/00 |
| | | | 700/91 |
| 2013/0108400 A1* | 5/2013 | Nogi | H01L 21/67276 |
| | | | 414/217 |
| 2013/0197981 A1* | 8/2013 | Vendetti | H04W 4/33 |
| | | | 705/14.5 |
| 2014/0153184 A1* | 6/2014 | Chang | G06F 1/20 |
| | | | 361/679.48 |
| 2014/0180711 A1 | 6/2014 | Kamen et al. | |
| 2017/0124365 A1* | 5/2017 | Shin | G01S 5/10 |
| 2017/0262955 A1* | 9/2017 | Lin | G09G 5/001 |
| 2019/0138767 A1* | 5/2019 | Swart | H02J 7/345 |
| 2019/0205941 A1* | 7/2019 | Sherman | G06Q 30/0271 |

OTHER PUBLICATIONS

Ginu Thomas, Review on FPGA Based Health Care System. (Year: 2014).*
Clyde Saldanha, The Journal on Information Technology in Healthcare. (Year: 2006).*
Sungmin Yi, Load Balancing for Real-time, Location-based Event Processing on Cloud Systems. (Year: 2013).*
Seol Young Jeong, Fully Distributed Monitoring Architecture Supporting Multiple Trackees and Trackers in Indoor Mobile Asset Management Application. (Year: 2014).*
International Searching Authority, "Search Report," issued in connection with PCT application PCT/US2017/069065, dated Apr. 27, 2018, 11 pages.
International Searching Authority, "Written Opinion," issued in connection with PCT application PCT/US2017/069065, dated Apr. 27, 2018, 6 pages.
International Searching Authority, "International Preliminary Report on Patentability," issued in connection with PCT application PCT/US2017/069065, dated Jul. 11, 2019, 8 pages.

* cited by examiner

RECEIVER HEALTH SYSTEMS AND METHODS FOR A REAL TIME LOCATION PLATFORM

CROSS-REFERENCE TO RELATED APPLICATIONS

This patent arises from a patent application claiming the benefit of U.S. Provisional Patent Application Ser. No. 62/441,201, which was filed on Dec. 31, 2016. U.S. Provisional Patent Application Ser. No. 62/441,201 is hereby incorporated herein by reference in its entirety. Priority to U.S. Provisional Patent Application Ser. No. 62/441,201 is hereby claimed.

FIELD OF THE DISCLOSURE

This disclosure relates generally to healthcare environments, and, more particularly, to methods and apparatus to facilitate proximity detection and location tracking.

BACKGROUND

Real-time location systems (RTLS) monitor asset distribution and usage, providing actionable information to help control costs and improve the quality and efficiency of care. Systems that have been developed to track and analyze activities in clinical settings have included installing Radio Frequency Identification (RFID) or infrared (IR) reader infrastructures into buildings to capture position information. RFID sensors may be placed on the people and/or assets that need to be tracked.

However, this is an expensive and time-consuming solution because it requires pulling power and data cabling to all the required locations. Location accuracy can also vary depending on technology. Typical RFID systems have a tolerance of approximately plus-or-minus ten feet, further limiting their range. RFID and IR-based sensors, though, are highly susceptible to drift due to interference in the environment (e.g., a patient room) and cross talk between locations that are physically separated, but have a line of sight between them (e.g., two patient rooms across the hall from each other).

Therefore, it would be desirable to design a system and method for tracking locations and interactions between people and assets in an environment with minimal infrastructure requirements and standardized technologies.

BRIEF SUMMARY

Certain examples provide improved systems, apparatus, methods, and media for real time location system management.

Certain examples provide an apparatus including a real time location system (RTLS) health processor. The example RTLS health processor includes an event processor to process an event included in a message from an RTLS device to identify event information related to the RTLS device, the event relating to a health of the RTLS device and the event information including an event type and an event detail. The example RTLS health processor includes a health analyzer to compare the event detail to a prescribed bound for the event type, the event relating to a health of the device. The example RTLS health processor includes an output generator to, when the event information is outside the prescribed bound, trigger a response to address the event with respect to the RTLS device.

Certain examples provide a computer-readable storage medium including instructions that, when executed, cause a processor to be configured to implement a real time location system (RTLS) health processor. The example RTLS health processor is to include an event processor to process an event included in a message from an RTLS device to identify event information related to the RTLS device, the event relating to a health of the RTLS device and the event information including an event type and an event detail. The example RTLS health processor is to include a health analyzer to compare the event detail to a prescribed bound for the event type, the event relating to a health of the device. The example RTLS health processor is to include an output generator to, when the event information is outside the prescribed bound, trigger a response to address the event with respect to the RTLS device.

Certain examples provide a processor-implemented method for a real time location system (RTLS). The example method includes processing, using a processor, an event included in a message from an RTLS device to identify event information related to the RTLS device, the event relating to a health of the RTLS device and the event information including an event type and an event detail. The example method includes comparing, using the processor, the event detail to a prescribed bound for the event type, the event relating to a health of the device. The example method includes, when the event information is outside the prescribed bound, triggering, using the processor, a response to address the event with respect to the RTLS device.

BRIEF DESCRIPTION OF THE DRAWINGS

The features and technical aspects of the system and method disclosed herein will become apparent in the following Detailed Description set forth below when taken in conjunction with the drawings in which like reference numerals indicate identical or functionally similar elements.

DETAILED DESCRIPTION

Figure 1:
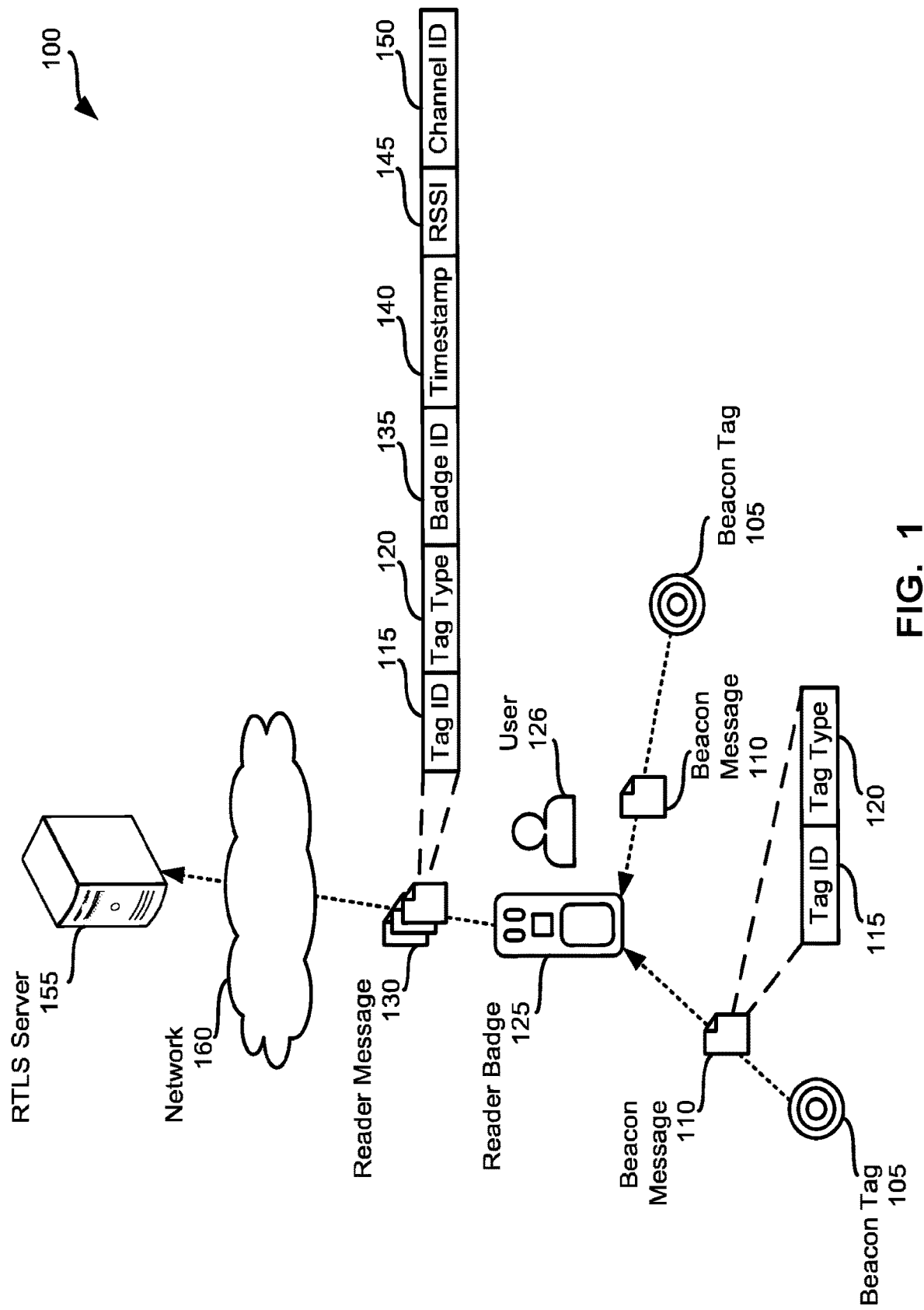
FIG. 1 is a block diagram illustrating an example environment constructed in accordance with the teachings of this disclosure to facilitate proximity detection and location tracking.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

I. Overview

Certain examples provide novel systems and associated methods that enable hospitals and/or other healthcare institutions to capture real time location data regarding their assets. Signals emitted by beacons, such as low-energy (e.g., Bluetooth Low Energy (BLE), etc.) beacons are captured by receivers. Software associated with the receivers captures, analyzes, and filters the collected location data, which can then be forwarded to a cloud-based server and associated software, which can facilitate crowd-sourcing to further analyze the data. Unlike other real-time location services using low-energy and/or other wireless communication (e.g., Wi-Fi, etc.), beacons can be tracked and data can be exchanged without opening ceilings or drilling walls to run cables in a lengthy, invasive installation. Instead, a wireless beacon-receiver tracking network can be configured in days, rather than months. Certain examples enable location tracking of equipment for inspection and preventative maintenance, equipment location for patient care, and analysis and insight into collected data regarding how, when, and how often equipment is used.

In certain examples, beacon-based data can be made available to users via Web-based interface and associated application. The Web-based interface can be accessible via a desktop computer, laptop, tablet computer, smart phone, etc. Location asset data can be integrated with other management system(s), for example.

Certain examples of the presently disclosed technology improve proximity detection and location tracking of resources in an environment such as a hospital. An example system disclosed herein includes one or more beacon tags affixed to assets within the environment and that transmit (e.g., periodically, aperiodically and/or as a one-time event) beacon messages. The beacon messages are received by a mobile reader badge that listens for beacon messages transmitted in the environment. For example, disclosed example reader badges (sometimes referred to herein as "readers," "badges" or "mobile wireless bridges") may include a network interface to receive beacon messages transmitted via low power Bluetooth Low Energy (BLE). In some disclosed examples, the reader badges process the received beacon messages and communicate information obtained from the beacon messages to one or more real-time location services (RTLS) servers via a communication infrastructure. For example, disclosed example reader badges may aggregate and communicate a batch of beacon messages (e.g., a threshold number of beacon messages, a threshold interval of time (e.g., a window of interest), etc.) to an RTLS server via a Wi-Fi infrastructure (e.g., a wireless network). In some disclosed examples, the RTLS server processes the received batch of beacon messages to facilitate real-time location tracking of the resources in the environment. In some disclosed examples, the RTLS server may report the location of resources via charts, graphs, tables, etc.

Real-time location services enable improved patient workflow via proximity detection and location tracking in a healthcare environment, such as a hospital. Location tracking can be used to locate resources such as mobile assets (e.g., patients, intravenous (IV) pumps, telemetry units, wheelchairs, etc.) within the hospital. For example, location tracking can be used to locate a "lost" or "missing" IV pump within a patient's room. Proximity detection facilitates an improved understanding of how interactions occur during the patient workflow. For example, based on the proximity to a soap dispenser, a user (e.g., a system administrator) can determine whether a caretaker washed their hands prior to interacting with a patient.

Example systems and methods disclosed herein facilitate improved proximity detection and location tracking by creating a hospital tracking network within the hospital using the communication infrastructure already installed in the hospital. Beacon tags are installed throughout a location or building. For example, beacon tags can be affixed to stationary assets (e.g., patient room entry ways, sinks, water fountains, hallways, etc.) and mobile assets such as hospital beds, IV pumps, soap dispensers, etc. In some disclosed examples, the beacon tags are also included in disposable patient tags provided to the patient upon admission of a hospital stay. Beacon tags are low-cost, low-power transmitters of beacon messages. A beacon message (sometimes referred to herein as a "beacon") includes information about the beacon tag such as a unique identifier (e.g., a tag identifier such as a media access control (MAC) address) and a tag type identifier (e.g., whether the beacon tag is affixed to a fixed-location asset or to a mobile asset). In some disclosed examples, the beacon tags broadcast (e.g., advertise, communicate, transmit, etc.) beacon messages at pre-set frequencies (e.g., ten times a second, once a second, once a minute, etc.). For example, a beacon tag affixed to a fixed-location asset (e.g., a sink) may broadcast beacon messages ten times a second, while a beacon tag affixed to a mobile asset (e.g., a wheelchair) may broadcast beacon messages at relatively shorter intervals (e.g., once a second).

A reader badge is a mobile wireless bridge that facilitates mobile tracking by "listening" and receiving beacon messages broadcast by beacon tags. The reader badge includes a BLE controller to receive connection-less beacon messages broadcast by beacon tags. The reader badge also includes a Wi-Fi controller to establish a connection with an RTLS server. The reader badge may be worn or transported by hospital caregivers. For example, a reader badge may be worn as a lanyard or clipped to the caregiver's clothing. As the caregiver moves about the hospital, the reader badge passively collects beacon messages and communicates reader messages to an RTLS server at the backend of the system. In some examples, the reader badge collects a number (e.g., a predetermined number) of beacon messages or waits a period (e.g., a predetermined period of time) prior to communicating the reader messages. In some examples, the reader badge generates and communicates a reader message as a beacon message from a beacon tag is received. A reader message includes information received from the beacon message such as a unique identifier of the source beacon tag and a spatial location of the source beacon tag. In some examples, the reader badge includes a timestamp identifying when the beacon message was received by the reader badge in the reader message. In some examples, the reader badge includes a received signal strength indication (RSSI) value (e.g., a power ratio in decibels of the measured power to one milli-watt (dBm)).

Example reader badges disclosed herein include a proximity engine to process the beacon messages and determine distance from the source (e.g., the beacon tag that broadcast the corresponding beacon message). For example, a hospital room may include a first beacon tag affixed to a door, a second beacon tag affixed to an infusion pump, a third beacon tag affixed to a bed, and a fourth beacon tag included in a patient tag (e.g., a disposable bracelet including patient identification information such as name, sex, date of birth information). As the caregiver moves about the hospital room, the reader badge may receive beacon messages from each of the beacon tags. The proximity engine can determine the RSSI strength for each of the beacon messages and associate RSSI strength with a respective beacon tag.

In some examples, the proximity engine determines which beacon tags are proximate (e.g., near or closely located) to the reader badge. For example, the proximity engine can compare the RSSI strength of a beacon message to a threshold and if the RSSI strength satisfies the threshold (e.g., the RSSI strength is greater than a threshold), the proximity engine identifies the source beacon tag as proximate to the reader badge. In some examples, the proximity engine discards beacon messages that are not proximate to the reader badge.

For example, fixed beacon receivers can be plugged into alternating current power outlets throughout a hospital. The beacon receivers capture transmissions from beacon tags moving around them and then forward the unique identifiers of those tags via the hospital's Wi-Fi network to a cloud-based server. Hospitals can view location information based on that data. The beacon tags can be attached to an asset and/or be worn by staff members or patients, for example.

In the example, mobile BLE receivers in the form of a badge device, similar to a pager, can be worn by clinical personnel. As with the fixed receivers, these badge devices also capture beacon transmissions and forward the data via the Wi-Fi network. The system can use big-data analytics and crowd-sourcing to expand the solutions range and real-time accuracy. Users can then use a Web-based application to easily find assets (e.g., the closest assets, all assets of one type, a specific device, etc.). For example, if a staff member were looking for a clean infusion pump, he or she could make a request via an application on his or her tablet and then access location data related only to items within the same zone in which they are located, for example.

Example systems and methods disclosed herein include an RTLS server that monitors and/or reports tracking location and interactions between people and assets in an environment. For example, the RTLS server can aggregate reader messages from the one or more reader badges included in an environment (e.g., the hospital). The RTLS server may be in connection with the reader badges via a wireless Intranet network (e.g., a wireless local area network, etc.) and/or a wireless Internet connection.

As healthcare assets continue to become smaller and more ergonomic, RTLS tracking with a small footprint becomes increasingly important. Additionally, as a hospital's inventory of healthcare equipment gets leaner, the equipment is likely to be cleaned more often. Therefore, an asset tracking beacon should withstand frequent, repeated cleaning with harsh disinfecting chemicals.

Certain examples provide an improved housing that can be applied with BLE and/or other location tracking technology to healthcare assets (e.g., scanner, IV pumps, monitors, etc.). In certain examples, a computerized maintenance management system (CMMS) and/or source system can organize and monitor assets and can remove and re-associate beacons from one asset to another asset on demand. Beacons can be installed on ergonomic items that do not have flat surfaces. Beacons can be developed with housings to withstand rigorous healthcare cleaning protocols while maintaining a small footprint to not disturb normal usage of equipment to which the beacon is applied.

A quality of location data provided by a real time location platform can depend on health of devices deployed to receive sensory and/or location events. If deployed devices are not functioning as intended, the location data produced by the system may be inaccurate/unreliable. To help ensure accurate location data, support teams can monitor system health, isolate problematic devices and correct the problems through reconfiguration/replacement/upgrades/etc.

Certain examples provide receiver health methods and systems for real time location platforms. Certain examples define a mechanism and associated application programming interface (API) specification by which location receivers deployed as part of a real time location platform can transmit system health information using an event-based messaging framework. The data/events provided can be captured and utilized to maintain the system and help ensure improved or optimal performance.

Devices used to implement a real time location platform may have numerous dependencies, including a reliable power supply (e.g., battery, outlet, etc.), network connectivity and acceptable environmental conditions (e.g. min/max operating temperature, etc.). With a large number of devices deployed, it is not feasible or cost effective to manually inspect each device in the field on a regular basis. Certain examples facilitate device self-reporting of health status and associated system events to help maintain a functioning system.

In certain examples, location devices are designed to submit event data (e.g., as JavaScript Object Notation (JSON) documents, etc.) to a service interface (e.g., a representational state transfer (REST) or RESTful service interface, etc.). There are numerous events defined, and these events can be sent in response to a condition (e.g., device regaining network connectivity, device placed on charger, device removed from charger, etc.) or on a time schedule that is configurable as part of the device profile. Events include a set of base (e.g., header, etc.) attributes that are used for ongoing system health management. In addition, each event includes a details section where attributes/data specific to an event type can be included.

In certain examples, receiver health includes a set of events defined for receiver devices (e.g., Bluetooth receiver devices, BLE receiver devices, etc.). The set of events can be defined according to an API, for example. In certain examples, a gateway client API includes a service interface specification or API for the RESTful service used by the device to post receiver health events, etc.

Certain examples provide a centralized health and monitoring capability for large scale systems that include a plurality of devices deployed in a wide range of environments. Without such monitoring, deployed systems may fall into disrepair over time and/or the costs of monitoring/maintaining such systems may threaten the commercial viability of the dependent products, for example.

Certain examples, when utilized, result in improved system performance, higher customer satisfaction, higher return on investment for the customer, lower cost of ownership for the customer, lower support costs for the supplier and increased profit margin for the supplier, etc.

Types and details of health events reported by devices can be extended/modified in a variety of ways to propose a "unique" set of health events. The mechanisms/protocols by which the events are delivered (e.g. JSON/XML/CSV or HTTP/JMS/SMTP, etc.) and/or captured can also be varied to propose a "unique" solution, for example.

II. Example Hospital Tracking Network

The foregoing systems and methods can be deployed to provide real-time location services. Real-time location services (RTLS) facilitate tracking people and assets in an industrial setting, such as a hospital. The example RTLS system described herein is designed to create location awareness of assets by capturing location and proximity information from beacon tags installed throughout the hospital. Examples disclosed herein utilize reader badges worn by healthcare workers (e.g., doctors, nurses, administrators, janitors, etc.) that receive beacon messages from beacon tags that are installed in and/or affixed to assets such as hallways, rooms, equipment, patients, etc. for which location and/or proximity information is to be collected between the beacon tags and the tagged asset. For example, the beacon tags may broadcast beacon messages including a unique identifier (e.g., a signature, a MAC address, a serial number, etc.) associated with the corresponding beacon tags. As the healthcare workers walk around the hospital, their reader badges collect beacon messages transmitted from beacon tags throughout the hospital. In some disclosed examples, the reader badges aggregate the beacon messages and transmit a batch of beacon messages to an RTLS server for processing. The example RTLS server disclosed herein processes the beacon messages to create location awareness through proximity and probability.

In some disclosed examples, beacon tags are installed in and/or attached to fixed-location (e.g., placed on stationary (or near stationary)) assets. For example, some "known location" beacon tags may be affixed to hallways, doors, windows, sinks, etc. As disclosed below, in some examples, the RTLS server utilizes the beacon messages received from "known location" beacon tags to determine a location for the reader badge.

In some disclosed examples, beacon tags are affixed to mobile assets such as equipment. For example, some "mobile location" beacon tags may be affixed to beds, wheelchairs, patients, etc. As disclosed below, in some examples, the RTLS server utilizes the beacon messages received from the "mobile location" beacon tags to determine what assets are near the corresponding reader badges (e.g., the reader badge that aggregated and transmitted a batch of beacon messages).

In addition, comparing the asset locations during different timestamp intervals may be useful in determining how the assets were moved and/or when caregivers interacted with the assets. For example, consider an example in which a wheelchair (e.g., a mobile-location asset) is located in a first patient room. In the illustrated example, assume that the wheelchair is affixed with a mobile-location asset beacon tag and that the first patient room is affixed with a fixed-location asset beacon tag. In the illustrated example, when a caregiver wearing a reader badge walks into the first patient room, their reader badge collects beacon messages broadcast by the wheelchair beacon tag and the first patient room beacon tag. In the illustrated example, the caregiver location is assigned to the first patient room based on the beacon messages broadcast by the first patient room beacon tag. In addition, since the wheelchair is "seen" in the same location, the wheelchair location may also be updated to the first patient room.

In the illustrated example, while the caregiver is in the first patient room, their reader badge collects beacon messages broadcast by the wheelchair beacon tag and the first patient room beacon tag. If the caregiver begins moving the wheelchair (e.g., from the first patient room to a second patient room), their reader badge will continue to collect beacon tags broadcast by the first patient room badge tag, but will also begin collecting beacon messages broadcast by a second patient room beacon tag. In the illustrated example, once the caregiver enters the second patient room, the caregiver location is updated to the second patient room. Additionally, in the illustrated example, since the wheelchair is still "seen" by the caregiver (e.g., the wheelchair location is determined to be proximate to the caregiver), the location of the wheelchair is also updated to the second patient room.

In the illustrated example, after the wheelchair is moved from the first patient room to the second patient room, confidence that the wheelchair is located in the second patient room rather than the first patient room may be low. However, in the illustrated example, each time a caregiver walks into the first patient room and does not "see" the wheelchair, confidence that the wheelchair is located in the first patient room decreases. Additionally, in the illustrated example, each time a caregiver walks into the second patient room and does "see" the wheelchair, confidence that the wheelchair is located in the second patient room increases. In the illustrated example, the "crowd" (e.g., the caregivers)

provides different snapshots of what is "seen" at different locations and at different times. As disclosed herein, an RTLS server may analyze the different snapshots to facilitate proximity detection and location tracking of assets in an environment.

Referring to FIG. 1, an example environment 100 in which examples disclosed herein may be implemented to facilitate proximity detection and location tracking using a mobile wireless bridge is illustrated. The example environment 100 of FIG. 1 includes example beacon tags 105, an example reader badge 125 and an example real-time location services (RTLS) server 155.

In the illustrated example of FIG. 1, the beacon tags 105 are implemented using low-power BLE transmitters and include a single coin-cell battery. In some examples, the single coin-cell battery provides power to the corresponding beacon tag 105 for two or more years. In the illustrated example, beacon tags 105 are installed throughout the environment 100 on two types of assets. For example, one or more beacon tag(s) 105 may be located on (e.g., affixed to) fixed-location assets such as doors, rooms, hallways, water fountains, etc. In addition, one or more beacon tag(s) 105 may be located on (e.g., affixed to) mobile-location assets such as patients (e.g., inserted within a patient tag), beds, IV pumps, wheelchairs, etc. Although the illustrated example of FIG. 1 includes only two beacon tags 105, other environments are likely to include additional beacon tags. For example, different environments may include tens, hundreds and/or thousands of beacon tags affixed to assets. In general, accuracy of the proximity detection and location tracking of assets in an environment is increased and/or decreased based on adding or reducing the number of beacon tags placed in the environment.

In the illustrated example of FIG. 1, the example beacon tags 105 periodically advertise their presence in the environment 100. For example, the beacon tags 105 may broadcast example beacon messages 110 every one second. In other examples, the beacon tags 105 may broadcast beacon messages 110 aperiodically and/or as a one-time event. In some examples, the beacon tags 105 may broadcast beacon messages 110 at different time intervals. For example, beacon tags 105 located on fixed-location assets may broadcast beacon messages 110 every two seconds, while beacon tags 105 located on mobile-location assets may broadcast beacon messages 110 every second. In some examples, beacon tags located on mobile-locations assets may broadcast beacon messages 110 at a first frequency (e.g., once every second) while the mobile-location asset is stationary and may broadcast beacon messages 110 at a second frequency (e.g., once every half-second) while the mobile-location asset is moving. However, other time intervals may additionally or alternatively be used.

In the illustrated example, the beacon messages 110 include tag identifying information 115 and tag-type identifying information 120. For example, tag identifying information 115 may be a unique identifier of the beacon tag 105 such as a MAC address, a serial number, an alphanumeric signature, etc. The example tag-type identifying information 120 identifies whether the beacon tag 105 broadcasting the beacon message 110 is affixed to a fixed-location asset or affixed to a mobile-location asset. However, the beacon messages 110 may include additional or alternative information. For example, the beacon messages 110 may include information identifying the software version being executed by the beacon tags 105, may include information identifying a power level of the beacon tag 105, etc.

In the illustrated example of FIG. 1, the beacon messages 110 are received by the reader badge 125. In the illustrated example, the reader badge 125 is worn by a hospital caregiver 126 such as a doctor, a nurse, etc. As the hospital caregiver moves through the hospital, the reader badge 125 collects beacon messages 110 broadcast by the beacon tags 105. For example, while the hospital worker 126 is visiting a patient in an example patient room #1, the example reader badge 110 may collect one or more beacon message(s) from a fixed-location asset beacon tag located on a door of the patient room #1, one or more beacon message(s) from a fixed-location asset beacon tag located on a sink in the patient room #1, one or more beacon message(s) from a mobile-location asset beacon tag located on the patient's identification tag, one or more beacon message(s) from a mobile-location asset beacon tag located on a bed in the patient room #1, etc.

In the illustrated example of FIG. 1, the reader badge 125 generates example reader messages 130 in response to receiving the beacon messages 110. For example, the reader badge 125 may create a reader message 130 including the tag identifying information 115 and the tag-type identifying information 120 included in the beacon message 110 and append example badge identifying information 135, an example timestamp 140, example signal strength information 145, and example channel identifying information 150. In the illustrated example, the badge identifying information 135 is a string of alphanumeric characters that uniquely identifies the reader badge 110 (e.g., a MAC address, a serial number, an alphanumeric signature, etc.). The example timestamp 140 identifies a date and/or time (e.g., Jan. 1, 2015, 9:10:04 pm) when the beacon message 110 was received by the reader badge 125. The example signal strength information 145 identifies signal strength of the beacon message 110 when it was received by the reader badge 125 (e.g., a received signal strength indication (RSSI) value). The example channel identifying information 150 identifies a channel on which the beacon message 110 was received (e.g., a Bluetooth frequency channel such as channel 37, channel 38 or channel 39).

In the illustrated example of FIG. 1, the reader badge 125 periodically communicates a group (e.g., a batch) of reader messages 130 to the RTLS server 155. For example, the reader badge 125 may transmit one or more reader messages 130 that were collected over a period of time (e.g., thirty seconds). Additionally or alternatively, the reader badge 125 may communicate one or more reader message(s) 130 aperiodically and/or as a one-time event. For example, the reader badge 125 may collect a threshold number of reader messages 130 prior to transmitting the collected reader messages 130 to the RTLS server 155. In some examples, the reader badge 125 transmits the reader messages 130 as they are created by the reader badge 125.

In the illustrated example of FIG. 1, the RTLS server 155 is a server and/or database that facilitates proximity detection and location tracking. In some examples, the RTLS server 155 is implemented using multiple devices. For example, the RTLS server 155 may include disk arrays or multiple workstations (e.g., desktop computers, workstation servers, laptops, etc.) in communication with one another.

In the illustrated example, the RTLS server 155 is in communication with the reader badge 125 via one or more wireless networks represented by example network 160. Example network 160 may be implemented using any suitable wireless network(s) including, for example, one or more data busses, one or more wireless Local Area Networks (LANs), one or more cellular networks, the Internet, etc. As used herein, the phrase "in communication," including variances thereof (e.g., communicates, in communication with, etc.), encompasses direct communication and/or indirect communication through one or more intermediary components and does not require direct physical (e.g., wired) communication and/or constant communication, but rather additionally includes communication at periodic or aperiodic intervals, as well as one-time events.

In the illustrated example of FIG. 1, the RTLS server 155 utilizes the reader messages 130 to facilitate proximity detection and location tracking of assets in the environment 100. In the illustrated example, the RTLS server 155 selects a portion of reader messages 130 received from the reader badge 125 to determine a location of the reader badge 125. For example, the RTLS server 155 may process the reader messages 130 to identify a first subset of reader messages 130 (e.g., one or more reader messages) that were received by the reader badge 125 during a first window of interest (e.g., a five second window) and that were fixed-location asset tag type (e.g., based on the tag-type information 120 included in the first subset of reader messages). In the illustrated example of FIG. 1, the RTLS server 155 utilizes the signal strength information 145 included in the first subset of reader messages 130 to determine a nearest fixed-location asset. For example, a relatively stronger RSSI value may indicate that the broadcasting beacon tag 105 is closer in proximity to the reader badge 125 than a beacon tag 105 associated with a relatively weaker RSSI value. In the illustrated example of FIG. 1, the RTLS server 155 updates the location of the reader badge 125 based on the nearest fixed-location asset.

In the illustrated example of FIG. 1, once the RTLS server 155 associates the reader badge 125 with a location (e.g., the location of the nearest fixed-location asset), the RTLS server 155 identifies a second subset of reader messages 130 (e.g., one or more reader messages) that were received by the reader badge 125 during the first window of interest (e.g., a five second window, etc.) and that were mobile-location asset tag type (e.g., based on the tag-type information 120 included in the second subset of reader messages 130). For example, the RTLS server 155 may update the location of a mobile-location asset based on its proximity to the reader badge 125.

In the illustrated example of FIG. 1, the RTLS server 155 selects a reader message of the second subset of reader messages 130 and classifies the corresponding mobile-location assets relative location to the reader badge 125 based on the RSSI value 155 included in the selected reader badge 130. For example, the RTLS server 155 classifies mobile-location asset as relatively-far assets when the signal strength information 155 satisfies a first threshold (e.g., the RSSI value is less than (−60) decibels, etc.). The example RTLS server 155 of FIG. 1 classifies mobile-location assets as relatively-immediate assets when the signal strength information 155 satisfies a second threshold (e.g., the RSSI value is greater than (−40) decibels, etc.). In the illustrated example of FIG. 1, the RTLS server 155 classifies mobile-location assets as relatively-near assets when the signal strength information 155 does not satisfy the first threshold and the second threshold. For example, the RTLS server 155 may classify mobile-location assets as relatively-near assets when the RSSI value is less than (−40) decibels and greater than (−60) decibels.

In the illustrated of FIG. 1, depending on the relative location classifications, the RTLS server 155 updates the location of the mobile-location asset and/or updates an asset-location confidence score associated with the mobile-location asset. In the illustrated example, the asset-location confidence score represents a probability (or likelihood) that a mobile-location asset may be found at the currently assigned asset-location. For example, when a mobile-location asset is "seen" in the same location, the RTLS server 155 increases the asset-location confidence score of the mobile-location asset. When the mobile-location asset is "seen" in a different location, the RTLS server 155 decreases the asset-location confidence score of the mobile-location asset. Additionally, when the asset-location confidence score fails to satisfy a location threshold (e.g., is less than a location threshold), the asset-location of the mobile-location asset may be updated based on, for example, the location of the reader badge 125 that collected the beacon message 110 emitted from the mobile-location asset (e.g., by the beacon tag 105 affixed to the mobile-location asset).

In the illustrated example, when a mobile-location asset is classified as relatively-far, the example RTLS server 155 of FIG. 1 discards the reader message 130 and the RTLS server 155 makes not change to the location of the mobile-location asset and/or the asset-location confidence score associated with the mobile-location asset. For example, the reader badge 125 may have collected a relatively weak beacon message emitted from a mobile-location asset passing through the hallway outside of the patient room #1. In some examples, the reader badge 125 may filter such beacon messages (e.g., beacon messages 110 that are associated with weak (e.g., low) RSSI values) rather than communicate the weak beacon messages to the RTLS server 155.

When a mobile-location asset is classified as a relatively-immediate asset, high signal strength (e.g., an RSSI value greater than (−40) decibels, etc.) may be indicative of a mobile-location asset that is in-front of the hospital worker 126, is being used by the hospital worker 126 and/or is being moved by the hospital worker 126. In some such instances, the location of the mobile-location asset may be assumed to be the same as the location of the reader badge 125. In the illustrated example, the example RTLS server 155 of FIG. 1 updates the location of the mobile-location asset to the location of the reader badge 125. In addition, the example RTLS server 155 increments the asset-location confidence score of the mobile-location asset (e.g., the probability of the mobile-location asset being located at the updated asset-location is increased). In some examples, if the beacon tag 105 is relatively-immediate to the reader badge 125, an assumption may be made that the caregiver is interacting with the corresponding assets. For example, the caregiver may be pushing a patient in a wheelchair.

In the illustrated example of FIG. 1, when a mobile-location asset is classified as a relatively-near asset (e.g., is associated with a medium signal strength), the example RTLS server 155 of FIG. 1 compares the current location associated with the mobile-location asset to the location of the reader badge 125. In the illustrated example, the RTLS server 155 increases the asset-location confidence score of the mobile-location asset when the current asset-location is the same as the location of the reader badge 125. For example, the mobile-location asset is "seen" in the same location as it is currently assigned. In some examples when the current asset-location is not the same as the location of the reader badge 125, the example RTLS server 155 decreases the asset-location confidence score of the mobile-location asset. In addition, the example RTLS server 155 compares the asset-location confidence score of the mobile-location asset to a location threshold and, when the asset-location confidence score fails to satisfy the location threshold (e.g., is less than the location threshold), the RTLS server 155 updates the asset-location of the mobile-location asset to the location of the reader badge 125 that received the corresponding beacon message 110.

In the illustrated example of FIG. 1, the example environment 100 includes an example dock module 165. The example dock module 165 may be used to charge one or more reader badges 125. In some examples, the dock module 165 receives beacon messages 110 from beacon tags 105 and/or transmits reader messages 130 to the RTLS server 155.

Figure 2:
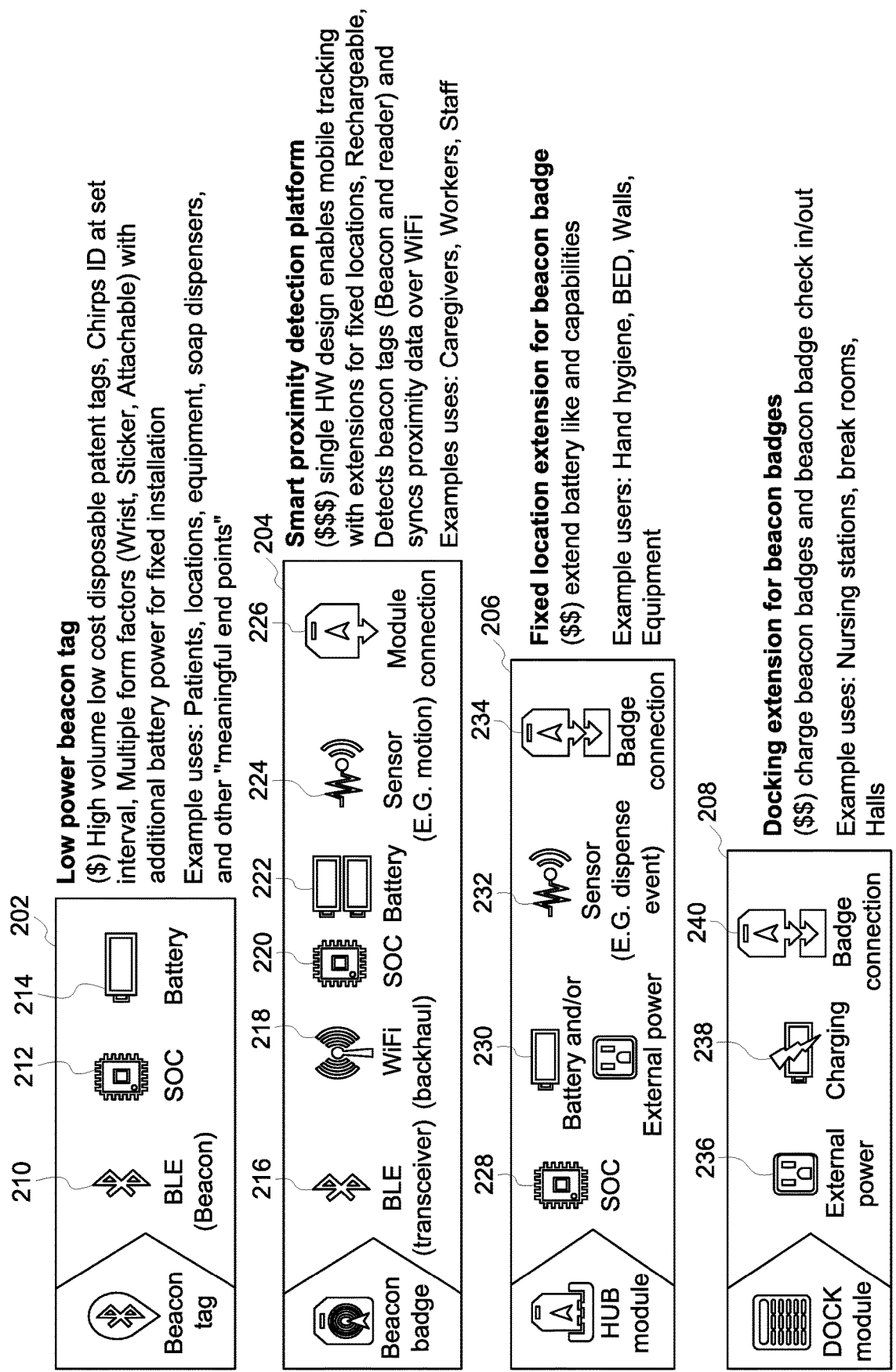
FIG. 2 is a block diagram of the example reader badge of the example environment of FIG. 1.

FIG. 2 illustrates various components included in an example beacon tag 202, an example beacon badge 204, an example hub module 206 and example dock module 208. For example, the beacon tag 202 includes one or more BLE chips (labeled "Beacon") 210 to transmit beacon messages 110, one or more power sources 214 (e.g., one or more coin-cell batteries) and a system-on-a-chip (SOC) 212 to manage the one or more BLE chips 210 and the one or more power sources 214. The example beacon badge 204 includes one or more BLE chips 216 (labeled "transceiver") to receive beacon messages 106a-109a, one or more Wi-Fi chips 218 to communicate with a wireless network (e.g., the example network 160), one or more power sources (e.g., one or more batteries) 222, one or more sensors 224 (e.g., a motion sensor, an accelerometer, a gyroscope, etc.) and a system-on-a-chip (SOC) 220 to manage the one or more BLE chips 216, the one or more Wi-Fi chips 218, the one or more power sources 222 and the one or more sensors 224. The example beacon badge 204 also includes an example module connector 226 to connect the beacon badge 204 to the example hub module 206 and/or the dock module 208.

In the illustrated example of FIG. 2, the beacon badge 204 is connectable to the example hub module 206. The connection between the beacon badge 204 and the hub module 206 may include a mechanical connection, an electrical connection, or combinations thereof. In the illustrated example, the hub module 206 may be used to track asset interactions with fixed locations. In a healthcare environment, examples of fixed locations include soap dispensers, beds, walls, equipment, etc. In other environments, such as a retail environment, fixed locations may include wall sconces, light fixtures, mirrors, shelving, and other such fixed locations.

The hub module 206 may be leveraged to identify particular locations. As an example, the beacon badge 204 may be coupled, via a badge connection 234, to a hub module 206 placed on an entrance to a restricted area to identify when a person wearing a beacon tag 202 enters (or approaches) the restricted area. In one embodiment, the hub module 206 includes a system-on-a-chip (SOC) 228 to manage components of the hub module 206, one or more power sources 230 (e.g., one or more batteries and an external power source (e.g., an AC/DC connection)) to extend the battery life and capabilities of the beacon badge 204, one or more sensors 232 communicatively coupled to the SOC 228, and a badge connection 234 for connecting the beacon badge 204 to the hub module 206.

In the illustrated example, the beacon badge 204 may be connectable (e.g., mechanically coupled, electronically coupled, etc.) to the example dock module 208. In the illustrated example, the dock module 208 may be used to charge one or more beacon badges 204. Accordingly, and in one embodiment, the dock module 208 includes an external power connector 236 (e.g., an AC connector), a charging indicator 238 to indicate whether the beacon badge 204 is charged or charging, and a badge connection 240 for connecting the beacon badge 204 to the dock module 208. In one embodiment, the dock module 208 is portable. For example, the dock module 208 may be placed throughout one or more environments, such as at cash registers, podiums, counters, nursing stations, break rooms, hallways, etc., and a caregiver may couple their beacon badge 204 to the dock module 208, via a badge connection 240, when they are off-duty.

Figure 3:
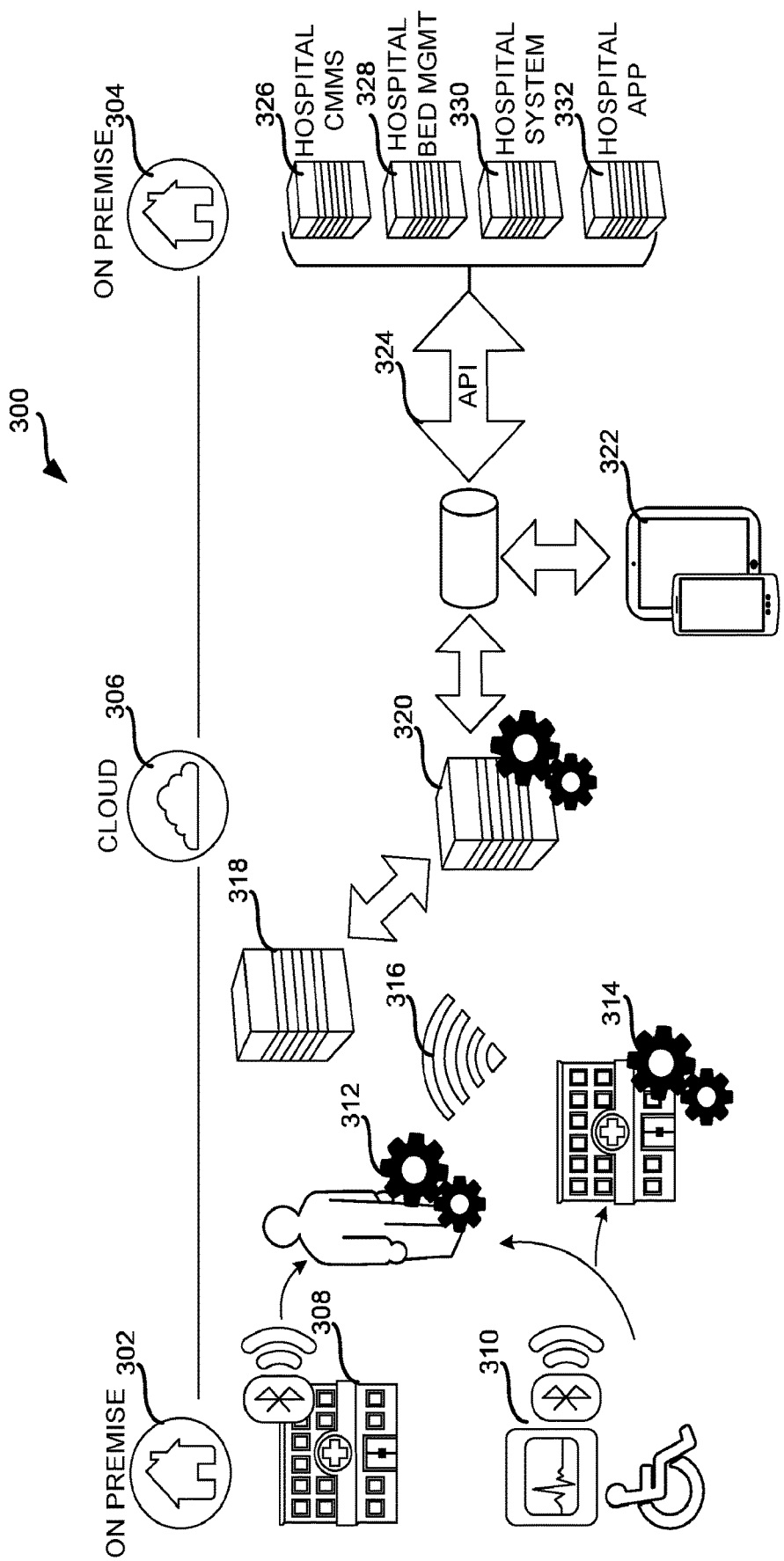
FIG. 3 illustrates an example environment illustrating interaction between premises via a cloud.

FIG. 3 illustrates an example environment 300 illustrating interaction between premises 302, 304 via a cloud 306. In the example of FIG. 3, one or more fixed beacons 308 and one or more mobile beacons 310 are positioned in a facility 302 (e.g., a hospital, clinic, etc.). The beacons 308, 310 are affixed (e.g., permanently affixed, removably affixed, etc.) to locations, assets, etc. For example, the fixed beacon 308 can be mounted on a wall at a location in the facility 302 at which asset(s) may be located to provide a location to a receiver. The mobile beacon 310 can be affixed (e.g., permanently, removably, etc.) to an item to be located and tracked (e.g., an intravenous (IV) pump, imaging scanner (e.g., x-ray, CT, ultrasound, etc.), crash cart, lab cart, etc.), for example.

The beacons 308, 310 are detected and read (e.g., via Bluetooth™, Bluetooth Low Energy (BLE), near field communication (NFC), etc.) by one or more mobile receivers 312 and/or fixed receivers 314, for example. For example, the mobile receiver 312 includes logic to process its location (e.g., with respect to the fixed beacon 308, etc.). The mobile receiver 312 can be worn by a person and/or mobile asset to create a crowdsourced environment in which the mobile receiver 312 interacts with beacons 308, 310 and informs the system 300 of the receiver 312 location and presence of beacon(s) 308, 310 within range of the location, for example. The fixed receiver 314 is configured with its location in the facility 302. The fixed receiver 314 can be mounted on a wall in a location where crowdsourcing is reduced (e.g., storage locations, enclosed locations, etc.) to interact with beacons 308, 310 and inform the system 300 of the receiver 314 location and presence of beacon(s) 308, 310 within range of the location, for example. The mobile receiver(s) 312 and fixed receiver(s) 314 process which asset(s) are located within range (e.g., as indicated mobile beacon(s) 310 and/or fixed beacon(s) 308, etc.) and notify other component(s) of the system 300.

The receiver(s) 312, 314 communicate over a channel 316, such as Wi-Fi, etc., with a middleware gateway 318 to transmit information regarding beacon 308, 310 location to a middleware engine 320. The middleware gateway 318 can be an edge device, gateway device, hub, and/or other electronic device to interface between the premises 302 and the cloud 306, for example. The middleware engine 320 can reside on the cloud 306 to process received beacon 308, 310 and receiver 312, 314 data and calculate location information. The middleware engine 320 can also publish location events to one or more receiving/subscribing recipients, for example.

For example, one or more consuming applications 322 access location data from the middleware engine 320 via the cloud 306 to leverage the location data for scheduling, tracking, (re)ordering, maintenance, billing, protocol compliance, treatment evaluation, employee evaluation, resource evaluation, and/or other resource management application(s), etc. Alternatively or in addition, an application programming interface (API) 324 provides location awareness data for consumption by one or more hospital applications 326-332 at a second facility (e.g., hospital, clinic, etc.) 304. For example, a hospital computerized maintenance management system (CMMS) 326, a hospital bed management system 328, and/or other hospital system 330, hospital application 332, etc., can receive and process asset location information via the API 324.

Figure 4:
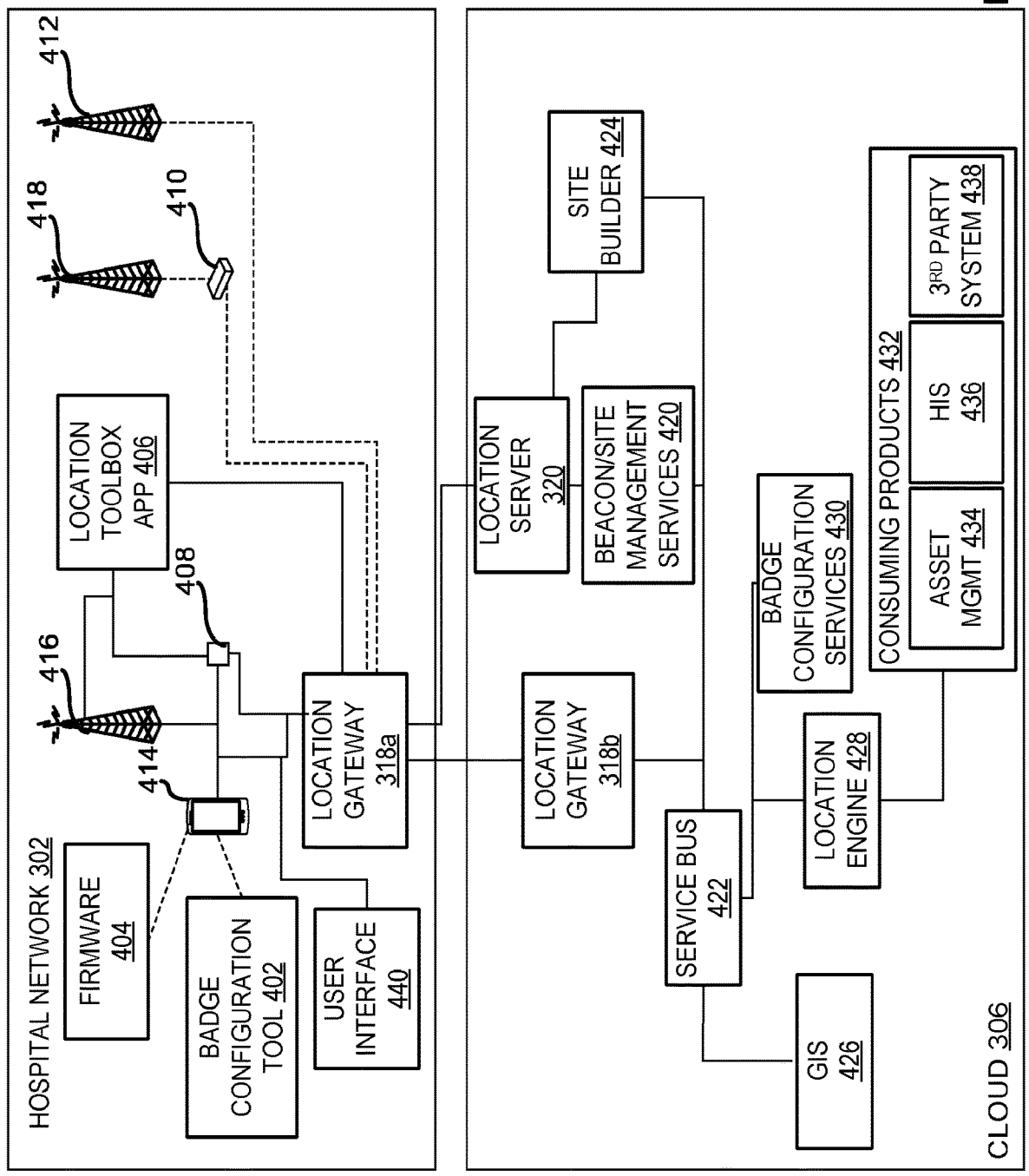
FIG. 4 illustrates an example architecture of the hospital network and the cloud of the example of FIG. 3.

FIG. 4 illustrates an example architecture 400 of the hospital network 302 and the cloud 306 of FIG. 3. As shown in the example of FIG. 4, the hospital network 302 communicates with the cloud 306 via the middleware or location gateway 318, which can be divided (as shown in the example of FIG. 4) into a client location gateway 318a and a server location gateway 318b. The example hospital network 302 includes a badge configuration tool 402 used to configure a badge 414 (e.g., a hospital staff badge, smart phone, etc.) for one or more parameters such as Wi-Fi network, gateway connectivity, gateway security credential/certificate, etc. The tool 402 can communicate with the badge 414 via Wi-Fi, Bluetooth, NFC, etc. Further, the badge 414 communicates with the client location gateway 318a to provide location information to the cloud 306.

Additionally, firmware 404 can communicate with the badge 414 to update firmware, settings, etc., on the badge 414. The example firmware 404 can provide and/or be associated with a software development kit (SDK) to enable integration of application(s) into the badge 414, for example. Using the SDK, the firmware 404 can provide notifications, offers, and/or other customizations to the badge 414 and/or a user/wearer of the badge 414, for example.

The example hospital network 302 of FIG. 4 also includes a location toolbox application 406, which communicates with a beacon 416 (e.g., a Bluetooth beacon, BLE beacon, etc.) and/or a hub 408 (e.g., via Bluetooth, BLE, etc.). The beacon 416 and/or hub 408 can also communicate with the badge 414 and/or the client location gateway 318a, for example. The toolbox 406 provides configuration and/or authorization application(s), setting(s), configuration(s), etc., for the hub 408, badge 414, and/or beacon 416, etc. For example, the toolbox 406 can be used to set beaconing frequency, beacon range, beacon transmission mode, etc. The toolbox 406, beacon 416, and/or badge 414 can communicate via the hub 408 with the client location gateway 318a, etc.

The example hospital network 302 of FIG. 4 can also include a passive reader 410, access point 412, and passive tag 418. The Wi-Fi access point 412 helps relay locating information by presence (e.g., in the facility 302), zone (e.g., in a particular area of the facility 302), location (e.g., actual location), etc. The passive tag 418 and passive reader 410 can interact to provide location information in the hospital network 302 to the client location gateway 318a, for example.

The client location gateway 318a communicates with the server location gateway 318b at the cloud 306. The client location gateway 318a also communicates with a middleware engine 320 such as a locationing server 320. The example server 320 provides a plurality of features including a management user interface (UI), a system health monitor, configuration information, insights/analytics, etc. The example server 320 communicates with beacon/site management services 420 and a site builder 424, which helps to map out a location (e.g., the hospital network 302, etc.) and beacons found at the location.

Using a service bus 422, the server location gateway 318b, beacon/site management services 420, and/or the site builder 424 can communicate with a geographic information system (GIS) 426 to create map(s) of the facility 302 to be stored using georeferenced location coordinates, for example. Fixed receivers placed in the facility 302 can be identified and added to the map using the site builder 424 and GIS 426. A location engine 428 can be used to leverage the map(s) and geographic information to associate location(s) with detected beacon events to derive a location for a particular asset, for example. Using the GIS 426 and site builder 424, maps can be modified/updated in real time (or substantially real time given some data processing, transmission, and/or storage latency, etc.) to make fast, fluid changes based on incoming data, for example. The GIS 426 provides spatial context to the inside of the facility 302 mapped by the site builder 424, for example. Using the GIS 426 platform, distance(s) between objects can be derived and georeferenced coordinates can be included. Information generated by the location engine 428 can be consumed by one or more products 432 including asset management 434, hospital information system (HIS) 436, and/or other third party system 438, etc. Badge configuration services 430 can also help with badge configuration on the server/cloud side, helping to update the badge configuration tool 402 at the hospital 302, for example.

In certain examples, a user interface device 440, such as a server, desktop computer, laptop computer, tablet computer, smart phone, and/or other computing device providing a graphical user interface (GUI) enables a Web-based and/or other console to be provided via the interface to one or more users. The user interface device 440 provides information, such as via a Web-based console and/or other GUI, etc., regarding connected local devices, such as beacons, badges, receivers, etc. Health status information such as heartbeat, location, MAC address and/or other device identifier (e.g., universally unique identifier (UUID), minor value, major value, etc.), firmware information, battery life, timestamp, signal strength, etc., can be viewed, interacted with, and/or otherwise modified, routed to another system/program, etc., via the user interface device 440, for example. The user interface device 440 can be a router, gateway, and/or other edge device such as gateway 318a, 318b, server 320, etc., and/or a separate device in communication with the hospital network 302 and/or cloud 306, for example.

Thus, certain examples provide systems and methods to monitor and manage badge(s), beacon(s), and receiver(s) and provide health statistics for such devices. Certain examples provide APIs that allow devices installed at a location to communicate status information to the cloud 306 infrastructure to be processed to display reports, analytics, facilitate interaction for repair/update, etc., to drive notifications, alerts, maintenance, etc., for system health and ongoing system operation. Certain examples facilitate monitoring and evaluation of network and system performance and retuning/reconfiguring/redefining desired network and/or system operation.

Figure 5:
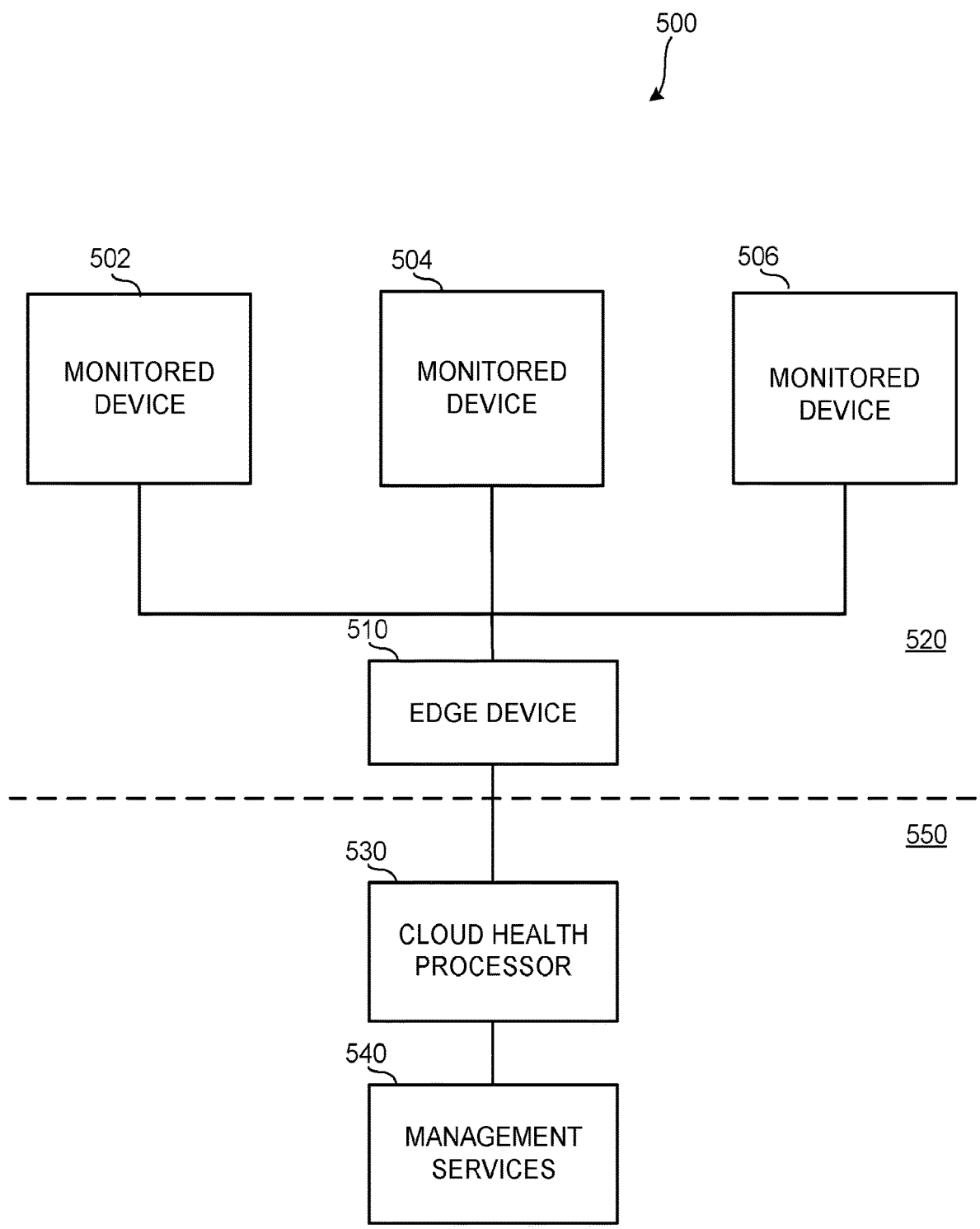
FIG. 5 illustrates a basic real time location platform including a number of monitored devices and an edge device in a facility, along with a cloud health processor and management service(s) in a cloud.

More generally, FIG. 5 illustrates a basic real time location platform 500 including a number of monitored devices 502-506 and an edge device 510 in a facility 520, along with a cloud health processor 530 and management service(s) 540 in a cloud 550. The monitored devices 502-506 can include one or more beacons, badges, and/or receivers 308, 310, 312, 314, 408, 410, 412, 414, 416, 418, etc. The edge device 510 can include the location gateway 318, etc. The cloud health processor 530 can include the location server 320, etc. The management services 540 can include beacon/site management services 420, badge configuration services 430, etc.

The cloud health processor 530 defines a mechanism and associated API specification by which location receivers 312, 314, 410 deployed as part of a real time location platform 300, 400 can transmit system health information using an event-based messaging framework. The data/events provided can be captured and utilized to maintain the system 300, 400 and help ensure optimal and/or otherwise improved performance.

In certain examples, given numerous dependencies, connectivity issues, and power concerns, the system 500 is configured such that the devices 502-506 self-report their health status and associated system events to the health processor 530 via the edge device 510 to help maintain a functional system 300, 400, 500. For example, location devices 502-506 are designed to submit event data (e.g., JSON documents, and/or other format/protocol such as XML, CSV, HTTP, JMS, SMTP, etc.) via the edge device 510 to an interface (e.g., a RESTful service interface, etc.) at or in communication with the health processor 530. In certain examples, the user interface device 440 can form part of the health processor 530 and/or be in communication with the health processor 530 to process and display device 502-506 health information.

A plurality of events can be defined. An event includes a set of base (e.g., header, etc.) attributes that are used for ongoing system health management. In addition, each event includes a details section in which attributes/data specific to an event type can be included. For example, numerous events can be defined, and these events can be sent in response to a specified condition (e.g., device regaining network connectivity, e.g., device placed on charger, e.g., device removed from charger, etc.) and/or on a time schedule that is configurable as part of the device profile. The following table provides some examples of receiver health-related events:

| Event | Occurrence/Trigger |
| --- | --- |
| On Charge | When a badge is placed on charge |
| Off Charge | When a badge is taken off charge |
| Forced Reboot | When the badge operating system restarts |
| Unforced Reboot/ System Error | When the badge operating restarts after a system error |
| Wi-Fi Reconnect | When the badge reconnects to Wi-Fi not associated with a reboot event |
| Heartbeat | When the receiver profile configured time interval has elapsed |

Thus, each receiver transmits health/operating details to the processor 530 via the API (e.g., API 324, etc.) when associated events are executed. In certain examples, a Wi-Fi reconnect does not include a roaming and/or access point transition for a mobile receiver. In certain examples, a heartbeat timer restarts on device reboot. In certain examples, a heartbeat interval is set to be frequent enough to monitor temperature changes, eliminating a need for temperature threshold events, for example. In certain examples, a beacon, badge, etc., can transmit similar health/operating details to the processor 530. In certain examples, a reason for reboot and/or associated error details (e.g., system error log, etc.) can be provided.

In certain examples, a service interface (e.g., API) specification can be provided, such as for a RESTful service, etc., used by device(s) 502-506 to post health events. The service interface can define a health API and/or a reference API that provides definition for location events, time, firmware updates, system health, receiver configuration, etc. For example, a location event request can be formatted as a JSON object to include a beacon MAC address, UUID, RSSI, battery life (e.g., percentage of battery life remaining, battery value, etc.), timestamp (e.g., a time at which the beacon event was received, etc.), receiver MAC address, etc.

A get time request can be implemented as a JSON formatted object including a time, such as a UNIX time, POSIX time, Epoch time, UTC time, etc., for example. A firmware update can be implemented as a binary file providing an application/octet stream to a target device 502-506, for example. A system health request can be implemented, for example, as a JSON formatted object including an event type, device MAC address, timestamp, firmware version, depth of discharge (e.g., percent of battery life remaining, etc.), temperature (e.g., device temperature in Fahrenheit, Celsius, etc.), details (e.g., any additional details provided for the event), etc. A receiver configuration request can be implemented, for example, as a JSON formatted object including a scan interval (e.g., a period of time for which received beacons are being evaluated to determine which beacons should be transmitted, etc.), a scan channel (e.g., BLE channel(s) on which the device should listen, etc.), heartbeat interval, Wi-Fi transmission frequency, profile name/ID, beacon type, proximity range, RSSI low (e.g., weakest RSSI signal strength considered within the range that a beacon should be processed, etc.), RSSI high (e.g., strongest RSSI signal strength considered within the range that a beacon should be processed, etc.), beacon hit count (e.g., a number of beacon hits required to be received within a scan interval, etc.), scan retention interval (e.g., a number of scans that occur before results of a scan are stored for transmission, etc.), send closest only (e.g., if true, all beacons received within the given range will be transmitted by the device, else only the closest (e.g., highest RSSI value) beacon is to be transmitted, etc.), suppress repeats (e.g., if true, transmissions from the device will be suppressed if they are the same as the previous scan interval, etc.), time service URL (e.g., uniform resource locator exposing the time service, etc.), event service URL (e.g., uniform resource locator exposing the event service, etc.), firmware service URL (e.g., uniform resource locator exposing the firmware service, etc.), firmware filename, etc.

The quality of location data provided by the real time location platform 300, 400 is dependent on the health of the devices deployed to receive sensory/location events. If the deployed devices are not functioning as intended, the location data produced by the system has the potential to be inaccurate/unreliable. To help ensure accurate location data, support system(s) and/or team(s) (e.g., health processor 530 and management service 540) must be able to monitor system health, isolate problematic devices and correct the problems through reconfiguration, replacement, upgrade, etc. Thus, certain examples provide a centralized health and monitoring capability for large scale systems that include many thousands of devices deployed in a wide range of environments. Without this system, deployed systems would fall into disrepair over time and/or the costs of monitoring/maintaining such systems would threaten the commercial viability of the dependent products. Certain examples monitor system health and provide maintenance/solutions to enable improved system performance, higher customer satisfaction, higher return on investment for a customer, lower cost of ownership for the customer, lower support costs for a supplier, increased profit margin for the supplier, etc.

In certain examples, the user interface device 440 (e.g., executed by and/or working in conjunction with the health processor 530, etc.) provides a plurality of views showing asset status information for a facility. For example, the interface 440 provides a Web-based device health console that includes a site overview providing information for some or all RTLS devices at the site. For example, an example GUI running on the interface device 440 can provide a site overview, fixed receiver view, mobile receiver view, fixed beacon view, mobile beacon view, and/or event view, etc.

The example overview provides a health overview of a gateway 318 and/or other edge device 510 through which health information is provided by monitored device(s) 502-506. For example, connection status, data routing travel time, event throughput, etc., can be measured and reported via the example console.

The example fixed receiver view provides heartbeat, anchor location, and firmware information for fixed receivers at the site, for example. The example fixed receiver view can be used to determine whether a fixed receiver is offline and to verify that fixed receivers have the correct firmware, for example. If a receiver has not sent a heartbeat to the gateway for a certain time interval (e.g., in the past hour, etc.), the receiver will show as offline. The offline status indicates that either the receiver cannot connect to the gateway or Wi-Fi or that the receiver has been unplugged, for example.

The example mobile receiver view provides heartbeat, battery, location, and firmware information for mobile receivers at the site, for example. The mobile receiver view can be used to determine whether a mobile receiver is offline and to verify that fixed receivers have the correct firmware, for example. If a receiver has not sent a heartbeat to the gateway for a certain time interval (e.g., in the past hour, etc.), the receiver will show as offline. The offline status indicates that either the receiver cannot connect to the gateway or Wi-Fi or that the receiver is out of battery, for example. The location of the receiver represents the last place that a fixed beacon saw the mobile receiver and the last time at which the mobile receiver was seen, for example.

The example fixed beacon view provides a fixed beacon MAC address, battery life remaining, anchor location, and timestamp and address of the last mobile receiver that saw the fixed beacon. If a fixed beacon has not been detected by a mobile receiver for a certain time interval (e.g., in the past hour, etc.), the beacon will show as offline. The offline status indicates that the beacon is masked from a receiver, the beacon is out of battery, or the closest receiver is out of battery, for example. The location of the beacon represents the last place that the mobile receiver saw the fixed beacon and a timestamp at which that sighting occurred, for example.

The example mobile beacon view provides a mobile beacon MAC address, battery life remaining, timestamp and address of the last receiver to see the mobile beacon, and information regarding the location of the fixed device (e.g., fixed receiver, fixed beacon, etc.) with respect to which the mobile beacon is positioned. If a mobile beacon has not been detected for a certain time interval (e.g., in the past hour, etc.), the beacon will show as offline. The offline status indicates that the beacon is masked from a receiver, the beacon is out of battery, or the closest receiver is out of battery, for example. The location of the beacon represents the last place that the receiver saw the fixed beacon and a timestamp at which that sighting occurred, for example.

The example event view provides a sensory event history for a chosen beacon or receiver. A timestamp represents a time at which a given sensory event occurred (e.g., between a beacon and a receiver, etc.). An RSSI represents a beacon's signal strength, and a major/minor value represents the beacon major and minor of the chosen beacon, for example.

Figure 6:
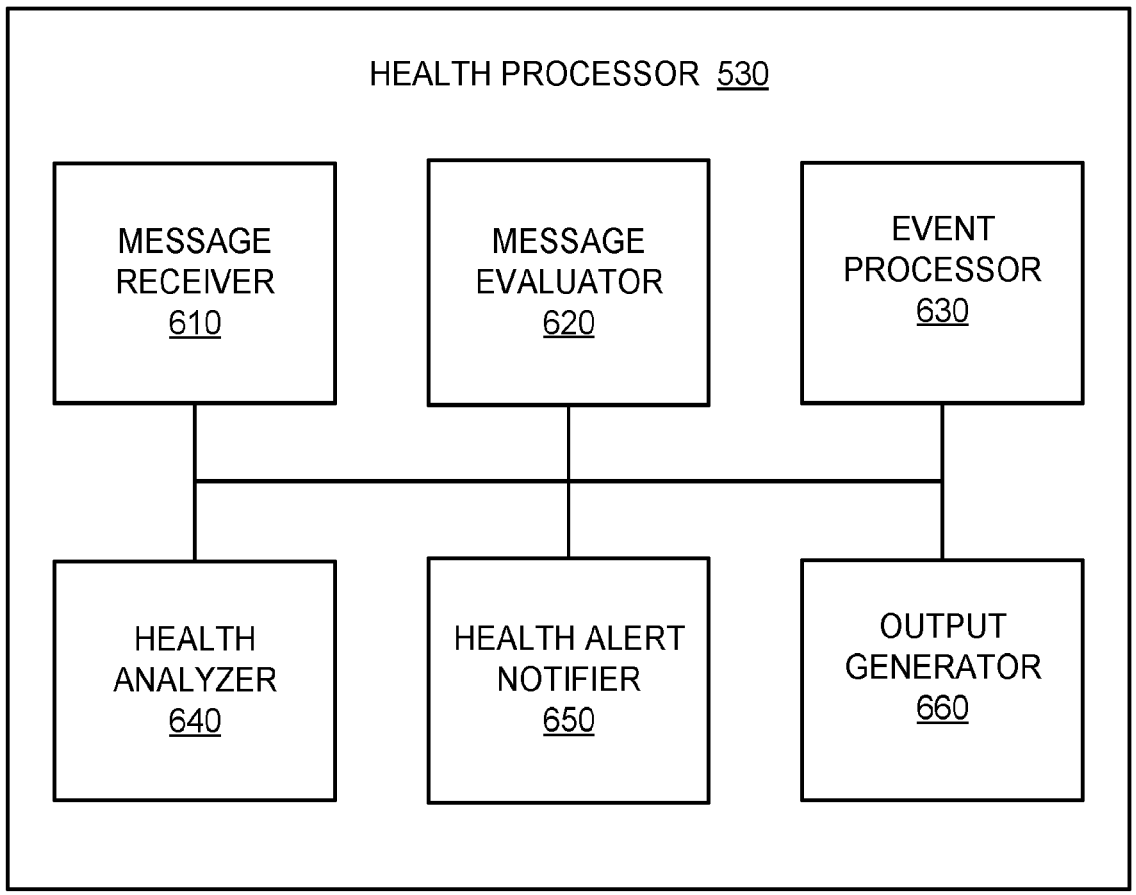
FIG. 6 illustrates an example implementation of the cloud health processor of FIG. 5.

FIG. 6 illustrates an example implementation of the cloud health processor 530. In the example of FIG. 6, the processor 530 includes a message receiver 610, a message evaluator 620, an event processor 630, a health analyzer 640, a health alert notifier 650, and an output generator 660.

The example message receiver 610 monitors for a message from a receiver (e.g., from one or more devices 502-506 including one or more beacons, badges, and/or receivers 308, 310, 312, 314, 408, 410, 412, 414, 416, 418, etc.). When a message is received, the example message evaluator 620 evaluates the received message to determine a message type associated with the message (e.g., location message, firmware message, time message, receiver configuration message, health message, etc.). If the message is not a receiver health message, then, the message evaluator 620 sends the message to another processor, such as the location engine 428, site builder 424, consuming product(s) 432, etc.

If the message is a health message, then the message evaluator 620 sends the message to the event processor 630. The example event processor 630 processes the health message to identify an event type indicated by the message. For example, the message may indicate an on charge event, off charge event, forced reboot event, unforced reboot/system error event, Wi-Fi reconnect event, heartbeat event, etc. Based on the event type, the event processor 630 processes the details of the event.

The event processor 630 provides the message details and event type to the health analyzer. Based on the event type, the example health analyzer 640 compares the details of the event to a threshold, range, standard, norm, etc. If the event is within normal or expected behavior, the event can be logged via the output generator 660. If the event is outside and/or otherwise deviates from the prescribed bound(s), the health alert notifier 650 can be triggered in response to the event. In some examples, the health alert notifier 650 can generate a response message or instruction to the device via the output generator 660 to adjust a level, setting, mode, etc., in response to the event (e.g., not charging enough, not charging properly, irregular heartbeat, reboot needed, etc.) such as to send a message to a user, automatically adjust a device setting, trigger a maintenance request, alert hospital staff to a failing device, change in setting/configuration warranted, etc. Thus, the output generator 660 can provide an update and/or other message to the device and/or a third party (e.g., beacon/site management services 420, badge configuration services 430, consuming product(s) 432, etc.) to repair, replace, and/or adjust the affected device(s). An alert, update, and/or other message can be generated to help ensure reliable operation and uptime of the RTLS system 300, 400, for example.

Figure 7:
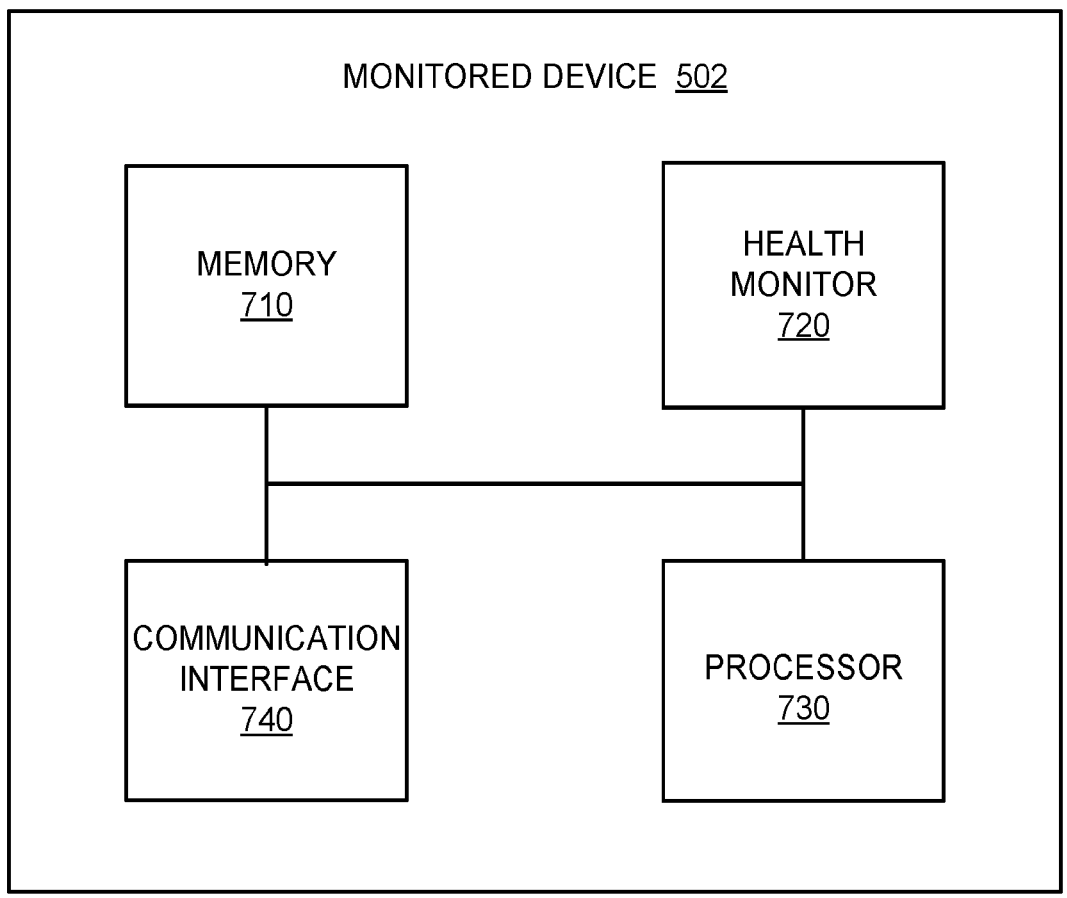
FIG. 7 illustrates an example implementation of a monitored device.

FIG. 7 illustrates an example implementation of the monitored device 502, 504, 506 (with the example monitoring device 502 shown in FIG. 7 for purposes of example illustration only). As described above, the monitored devices 502-506 can include one or more beacons, badges, and/or receivers 308, 310, 312, 314, 408, 410, 412, 414, 416, 418, etc. In the example of FIG. 7, the monitored device 502 includes a memory 710, a health monitor 720, a processor 730, and a communication interface 740.

The example memory 710 stores identification data for the device 502 as well as instructions for execution by the processor 730 of the device 502. The memory 710 can store status and/or other health information for the device 502 as determined by the health monitor 720, for example.

The example message receiver 610 monitors for a message from a receiver (e.g., from one or more devices 502-506 including one or more beacons, badges, and/or receivers 308, 310, 312, 314, 408, 410, 412, 414, 416, 418, etc.). When a message is received, the example message evaluator 620 evaluates the received message to determine a message type associated with the message (e.g., location message, firmware message, time message, receiver configuration message, health message, etc.). If the message is not a receiver health message, then, the message evaluator 620 sends the message to another processor, such as the location engine 428, site builder 424, consuming product(s) 432, etc.

If the message is a health message, then the message evaluator 620 sends the message to the event processor 630. The example event processor 630 processes the health message to identify an event type indicated by the message. For example, the message may indicate an on charge event, off charge event, forced reboot event, unforced reboot/system error event, Wi-Fi reconnect event, heartbeat event, etc. Based on the event type, the event processor 630 processes the details of the event.

The event processor 630 provides the message details and event type to the health analyzer. Based on the event type, the example health analyzer 640 compares the details of the event to a threshold, range, standard, norm, etc. If the event is within normal or expected behavior, the event can be logged via the output generator 660. If the event is outside and/or otherwise deviates from the prescribed bound(s), the health alert notifier 650 can be triggered in response to the event. In some examples, the health alert notifier 650 can generate a response message or instruction to the device via the output generator 660 to adjust a level, setting, mode, etc., in response to the event (e.g., not charging enough, not charging properly, irregular heartbeat, reboot needed, etc.) such as to send a message to a user, automatically adjust a device setting, trigger a maintenance request, alert hospital staff to a failing device, change in setting/configuration warranted, etc. Thus, the output generator 660 can provide an update and/or other message to the device and/or a third party (e.g., beacon/site management services 420, badge configuration services 430, consuming product(s) 432, etc.) to repair, replace, and/or adjust the affected device(s). An alert, update, and/or other message can be generated to help ensure reliable operation and uptime of the RTLS system 300, 400, for example.

Figure 8:
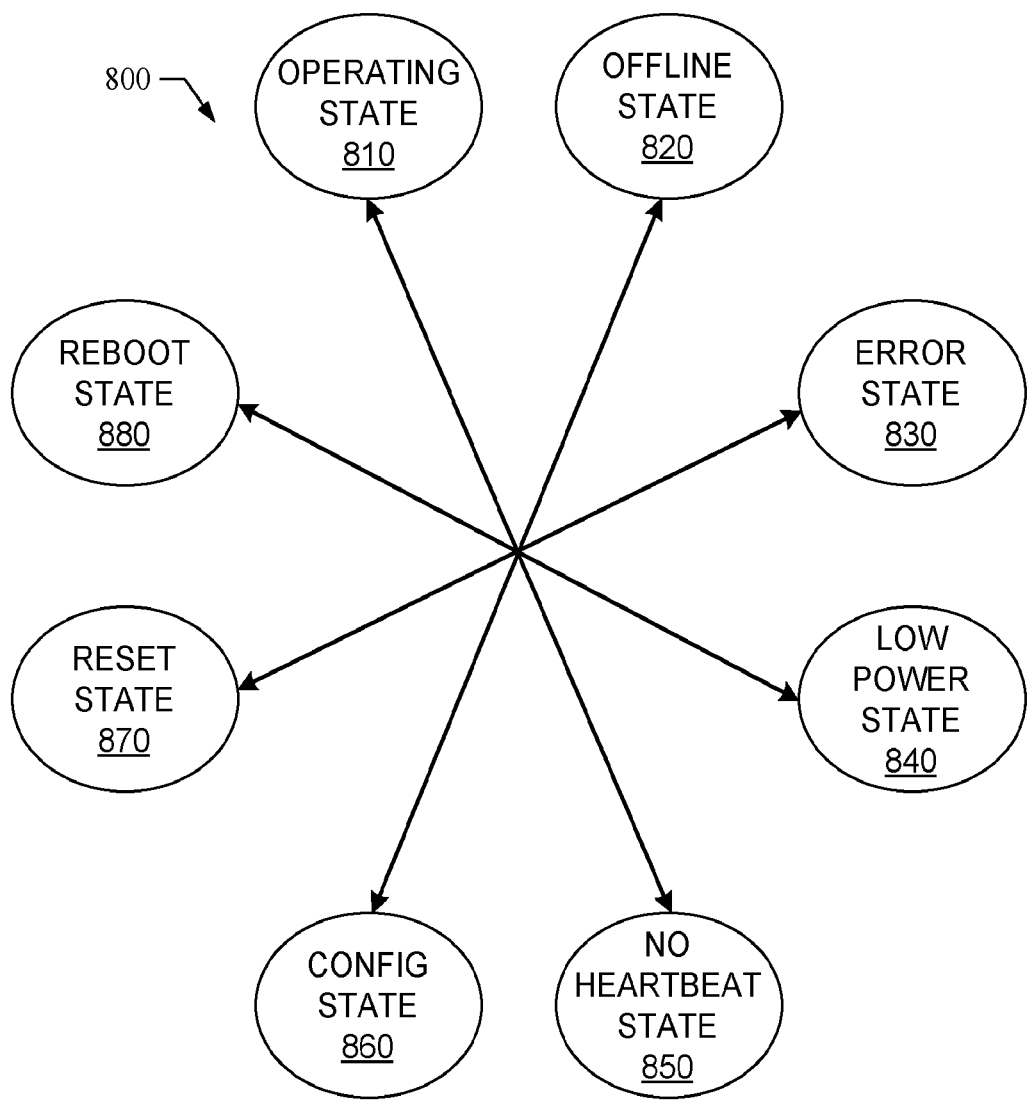
FIG. 8 depicts an example state diagram illustrating example health states of a monitored device.

FIG. 8 depicts an example state diagram 800 illustrating example health states of a monitored device 502-506. The example state diagram 800 can be stored as a state machine to alter the memory 710 and configure the processor 730 as directed by the health monitor 720 of the device 502-506, for example. As shown in the example of FIG. 8, a plurality of states can include an operating state 810, offline state 820, error state 830, low power state 840, no heartbeat state 850, configuration state 860, reset state 870, reboot state 880, etc. The monitored device 502-506 can transition among states 810-880 according to the example state machine 800.

For example, the monitored device 502-506 can transition to the operating state 810 when operating normally according to its configuration. The monitored device 502-506 can transition to the offline state 820 when the device 502-506 cannot find a network connected (e.g., to a gateway, Wi-Fi, etc.), for example. The monitored device 502-506 can transition to the error state 830 when it detects a problem with its operation, an issue/error outside its defined states, etc. The monitored device 502-506 can transition to the low power state 840 when the battery of the device 502-506, available wall outlet power, etc., is running low on power, for example. The monitored device 502-506 can transition into the no heartbeat state 850 when it has not detected another device's heartbeat for a certain time interval, for example.

The monitored device 502-506 can transition into the configuration state 860 when the monitored device 502-506 is being configured and/or otherwise set up in its configuration mode. For example, a technician can set up the monitored device 502-506 in configuration mode. The health processor 530, gateway 318 (e.g., 318a and/or 318b, etc.), another device 502-506, etc., can trigger the configuration state 860 at the monitored device 502-506 to adjust parameter(s)/setting(s) of the device 502-506, for example.

The monitored device 502-506 can transition into the reset state 870 when instructed to reset its settings to its default settings, for example. For example, a technician, health processor 530, gateway 318, another device 502-506, etc., can trigger the reset state 870 to reset the monitored device 502-506 to its factory default. The monitored device 502-506 can transition into the reboot state 880 when a reboot is triggered for the device 502-506 (e.g., by a technician, health processor 530, gateway 318, another device 502-506, etc.), for example.

Figure 9:
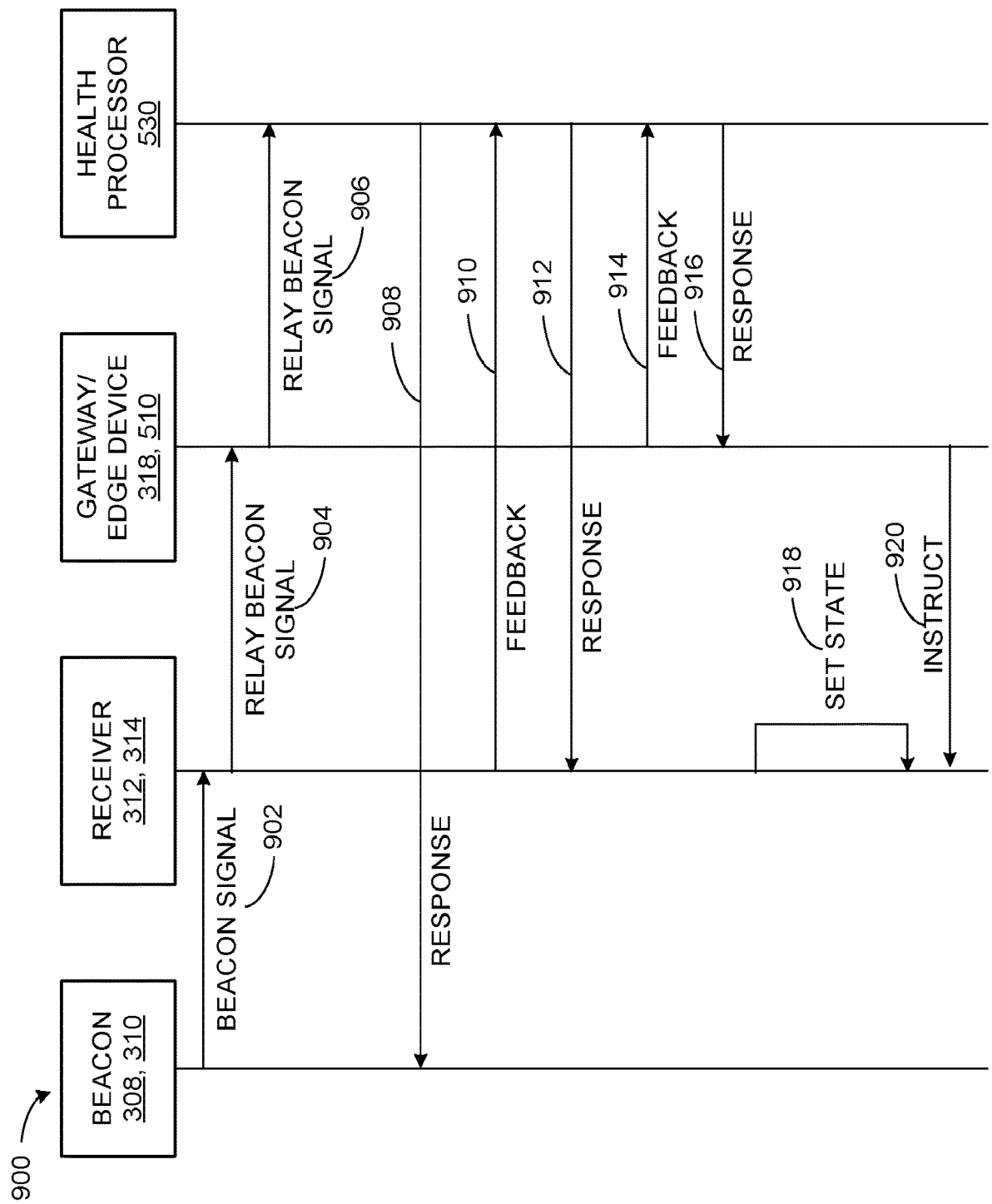
FIG. 9 shows an example data flow between a beacon, a receiver, and a cloud health processor via a gateway.

FIG. 9 shows an example data flow 900 between a beacon (e.g., a fixed 308 or mobile beacon 310, etc.), a receiver (e.g., a fixed 314 or mobile receiver 312, etc.), and the cloud health processor 530 via the gateway 318. At 902, the beacon 308, 310 provides a signal (e.g., a heartbeat, a ping, a status signal, etc.) within its range. For example, the beacon 308, 310 broadcasts a signal in its communication range to identify itself and provide its status.

At 904, the receiver 312, 314 relays the beacon signal to the gateway 318/edge device 510. For example, the receiver 312, 314 receives the beacon signal when in range of the beacon 308, 310 and packages information from the received beacon signal and generates a communication for the gateway 318/edge device 510.

In certain examples, the gateway 318/edge device 510 can process and react to the beacon signal data from the receiver 312, 314 (e.g., by logging the beacon signal data, generating a response (e.g., configuration, reset, reboot, error, acknowledgement, etc.) to return to the receiver 312, 314 (and/or through the receiver 312, 314 to the beacon 308, 310). In other examples, at 906, the gateway 318/edge device 510 relays the message from the receiver 312, 314 to the health processor 530. At 908, the health processor 530 generates a response (e.g., configuration, reset, reboot, error, acknowledgement, etc.) to return, via the gateway 318/edge device 510, to the receiver 312, 314 (and/or through the receiver 312, 314 to the beacon 308, 310).

At 910, if the receiver 312, 314 receives no beacon signal, then the receiver 312, 314 provides feedback to the gateway 318/edge device 510 to be routed to the health processor 530 regarding the missing/unavailable/offline/erroring beacon 308, 310, for example. At 912, the health processor 530 (and/or its gateway 318/edge device 510, etc.) can log the information and generate a response (e.g., to the receiver 312, 314, to the gateway 318/edge device 510, to the beacon 308, 310, to a service request, etc.).

At 914, if the gateway 318/edge device 510 receives no receiver communication, then the gateway 318/edge device 510 to can trigger a response and/or send an alert to the health processor 530 regarding the missing/unavailable/offline/erroring receiver 312, 314, for example. At 916, the health processor 530 (and/or its gateway 318/edge device 510, etc.) can log the information and generate a response (e.g., to the receiver 312, 314, to the gateway 318/edge device 510, to a service request, etc.).

At 918, if the receiver 312, 314 receives no gateway/edge device communication, then the receiver 312, 314 can enter an offline 820 or error 830 state, for example, until, at 920, receiving an instruction such as a reset, reboot, heartbeat communication from the gateway 318/edge device 510, etc.

While example implementations of the systems 100, 300, 400, 500 are illustrated in FIGS. 1-9, one or more of the elements, processes and/or devices illustrated in FIGS. 1-9 may be combined, divided, re-arranged, omitted, eliminated and/or implemented in any other way. Further, the example components of FIGS. 1-9 can be implemented by hardware, software, firmware and/or any combination of hardware, software and/or firmware. Thus, for example, any of the example components of FIGS. 1-9 can be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example components of FIGS. 1-9 is/are hereby expressly defined to include a tangible computer readable storage device or storage disk such as a memory (e.g., a read only memory (ROM), hard drive, flash memory, other volatile and/or non-volatile memory, etc.), a digital versatile disk (DVD), a compact disk (CD), a Blu-ray disk, etc. storing the software and/or firmware. Further still, the example systems of FIGS. 1-9 can include one or more elements, processes and/or devices in addition to, or instead of, those illustrated in FIGS. 1-9, and/or may include more than one of any or all of the illustrated elements, processes and devices.

Figure 10:
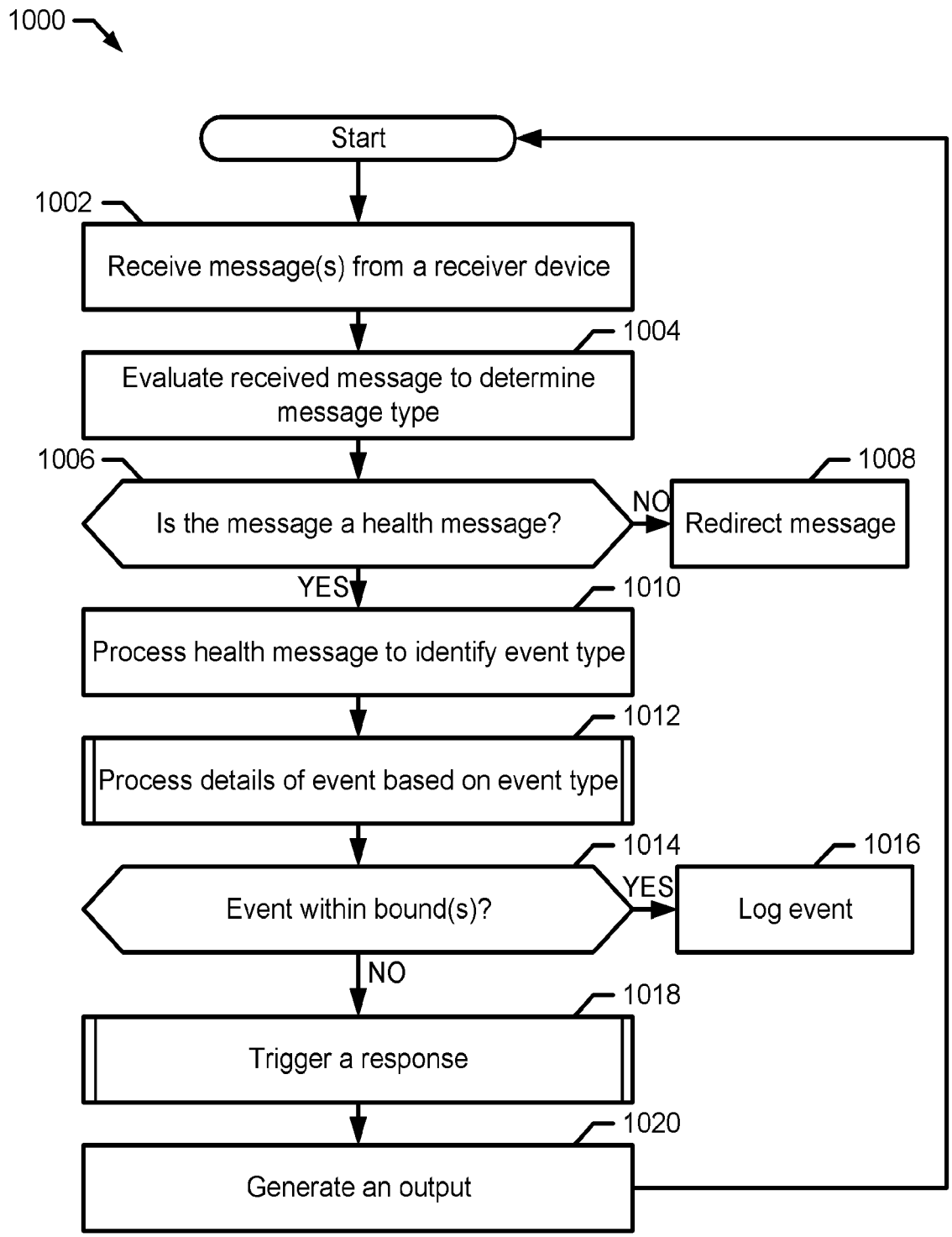
FIGS. 10-12 illustrates a flow diagram of an example method to monitor receiver and/or other device health in a real time location system.
Figure 11:
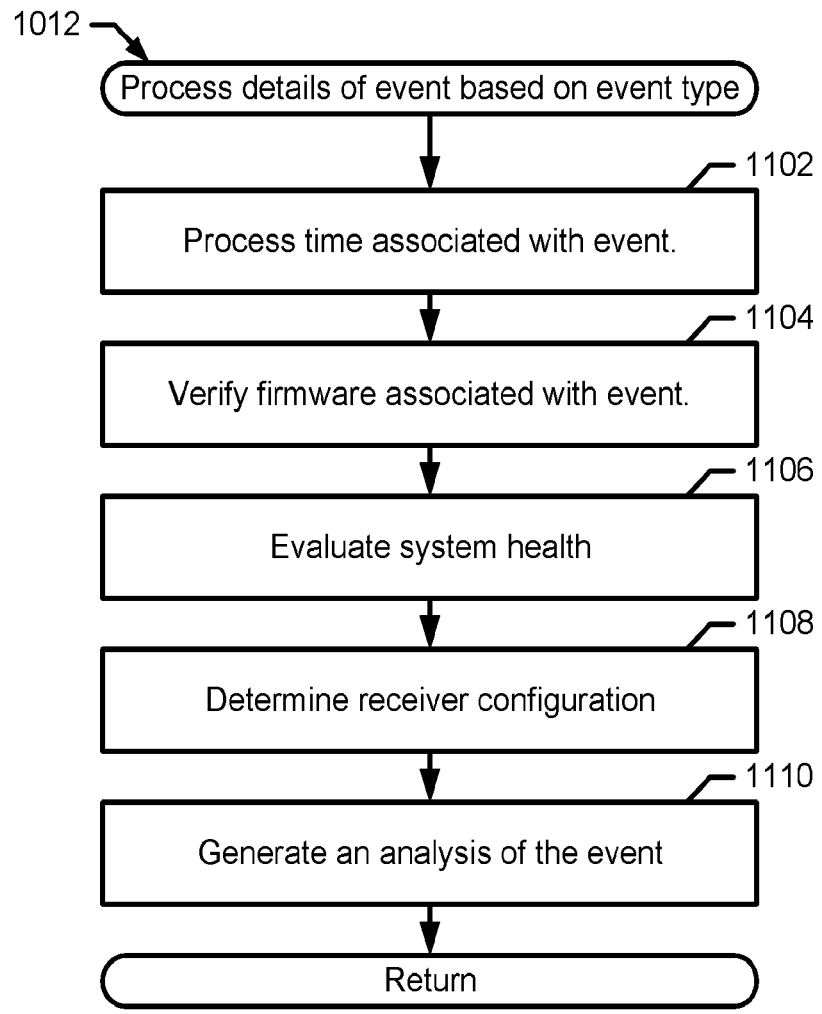
Figure 12:
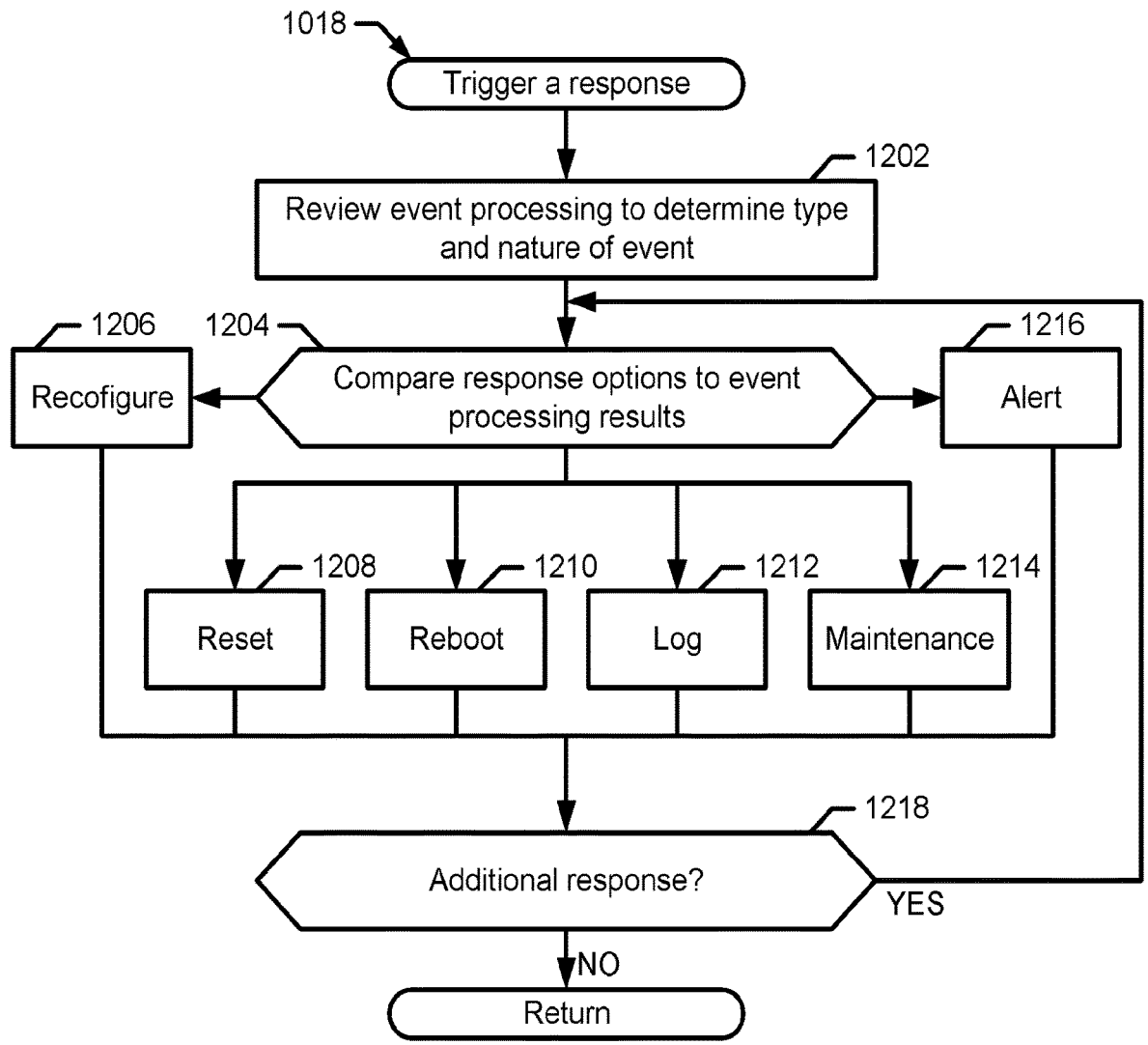

Flowcharts representative of example machine readable instructions for implementing the systems, states, and data flows of FIGS. 1-9 are shown in FIGS. 10-12. In these examples, the machine readable instructions comprise program(s) for execution by a processor such as the processor 1312 shown in the example processor platform 1300 discussed below in connection with FIG. 13. The program(s) can be embodied in software stored on a tangible computer readable storage medium such as a CD-ROM, a floppy disk, a hard drive, a DVD, a Blu-ray disk, or a memory associated with the processor 1312, but the entire program and/or parts thereof can alternatively be executed by a device other than the processor 1312 and/or embodied in firmware or dedicated hardware. Further, although the example program(s) are described with reference to the flowcharts illustrated in FIGS. 10-12, many other methods of implementing the example systems may alternatively be used. For example, the order of execution of the blocks may be changed, and/or some of the blocks described may be changed, eliminated, or combined.

As mentioned above, the example process(es) of FIGS. 10-12 can be implemented using coded instructions (e.g., computer and/or machine readable instructions) stored on a tangible computer readable storage medium such as a hard disk drive, a flash memory, a ROM, a CD, a DVD, a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) of FIGS. 10-12 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 10 illustrates a flow diagram of an example method 1000 to monitor receiver and/or other device health in a real time location system. At block 1002, messages are monitored to detect a message from a receiver. For example, the example message receiver 610 monitors for a message from a receiver (e.g., from one or more devices 502-506 including one or more beacons, badges, and/or receivers 308, 310, 312, 314, 408, 410, 412, 414, 416, 418, etc.). At block 1004, when a message is received, the message is evaluated to determine a message type. For example, the example message evaluator 620 evaluates the received message to determine a message type associated with the message (e.g., location message, firmware message, time message, receiver configuration message, health message, etc.). At block 1006, the message type is compared to a health message type. If the message is not a health message, then, at block 1008, the message is redirected for further processing. For example, when the message is not a receiver health message, the message evaluator 620 sends the message to another processor, such as the location engine 428, site builder 424, consuming product(s) 432, etc.

If the message is a health message, then, at block 1010, the health message is processed to identify an event type indicated by the health message. For example, the message evaluator 620 sends the message to the event processor 630. The example event processor 630 processes the health message to identify an event type indicated by the message. For example, the message may indicate an on-charge event, off-charge event, forced reboot event, unforced reboot/system error event, Wi-Fi reconnect event, heartbeat event, etc. At block 1012, based on the event type, the event processor 630 processes the details of the event. For example, the event processor 630 digests information associated with the event type and additional details if provided in the message.

At block 1014, the event is compared to prescribed bound(s) for the event. For example, the event processor 630 provides the message details and event type to the health analyzer. Based on the event type, the example health analyzer 640 compares the details of the event to a threshold, range, standard, norm, etc. At block 1016, if the event is within normal or expected behavior, the event is logged. For example, the event can be logged via the output generator 660. At block 1018, if the event is outside and/or otherwise deviates from the prescribed bound(s), a response to the event is triggered. For example, the health alert notifier 650 can be triggered in response to the event. In some examples, the health alert notifier 650 can generate a response message or instruction to the device via the output generator 660 to adjust a level, setting, mode, etc., in response to the event (e.g., not charging enough, not charging properly, irregular heartbeat, reboot/reset needed, reconfiguration warranted, etc.) such as to send a message to a user, automatically adjust a device setting, trigger a maintenance request, alert hospital staff to a failing device, change in setting/configuration warranted, etc. At block 1020, an output is provided. For example, the output generator 660 can provide an update and/or other message to the device and/or a third party (e.g., beacon/site management services 420, badge configuration services 430, consuming product(s) 432, etc.) to repair, replace, and/or adjust the affected device(s). An alert, update, and/or other message can be generated to help ensure reliable operation and uptime of the RTLS system 300, 400, for example.

FIG. 11 provides further detail regarding an example implementation of processing an event based on the identified event type (block 1012 of the example of FIG. 10). At block 1102, a time associated with the event is processed. For example, the received message for the event can include a time associated with the event that is processed by the event processor 630 to determine a timestamp associated with the event and/or a related message, a time since last response, time since heartbeat, etc.

At block 1104, firmware is verified. For example, the received message for the event can include an indication of firmware version for the associated device 502-506, and the event processor 630 can determine whether or not the device 502-506 has the latest and/or proper firmware.

At block 1106, system health is evaluated. For example, the event processor 630 and/or health analyzer 640 can evaluate event contents to determine an error code, indication of device 502-506 state, time since epoch, device battery life remaining, device temperature, and/or other event detail to determine a system health of the device 502-506 (e.g., a receiver, etc.).

At block 1108, receiver configuration is determined. For example, the health processor 530 can stored receiver configuration information, which can then be analyzed and compared to the evaluation of the system health and other event information such that the event processor 630, health analyzer 640, etc., of the health processor 530 can determine whether the receiver configuration is contributing to and/or otherwise causing the event, an adjustment to the receiver configuration can remedy an issue associated with the event, etc.

At block 1110, an analysis of the event is generated based on the time, firmware verification, system health evaluation, and receiver configuration determination. For example, the health processor 530 and its components can analyze the event based on timing (e.g., time of occurrence, time since last contact, time interval, etc.), firmware (e.g., old version, incorrect/inapplicable version, etc.), system health, receiver configuration, etc., to develop an understanding of the event, an impact of the event, and potential next action(s) for the event. For example, the analysis of the event by the event processor 630 can determine whether or not the event fits within expected, allowed, and/or other operational bounds for the receiver, that type of event, etc. Control can then return to block 1014 at which the event is determined to be within or outside its bounds, or example.

Thus, in certain examples, each receiver sends details regarding its system health to an API hosted by the edge device 510 and/or health processor 530 based on execution of certain events (e.g., on-charge, off-charge, forced reboot, unforced reboot/system error, network reconnect, heartbeat, etc.), and the health processor 530 can evaluate such health details to determine a response/next action, etc.

FIG. 12 provides further detail regarding an example implementation of triggering a response to the event (block 1018 of the example of FIG. 10). At block 1202, the processing of the event is reviewed to determine the type and nature of the event. For example, the event is reviewed by the health processor 530 to determine whether the event affects the operation of a receiver, an edge device, beacon, etc., such as an unresponsive receiver, a receiver not getting a beacon signal, a receiver having low battery, a receiver recently rebooted, etc.

At block 1204, available options for response are compared against results of the event processing to determine a most appropriate available response or responses. For example, the output generator 660 can provide an update and/or other message to the device and/or a third party (e.g., beacon/site management services 420, badge configuration services 430, consuming product(s) 432, etc.) to repair, replace, and/or adjust the affected device(s). An alert, update, and/or other message can be generated to help ensure reliable operation and uptime of the RTLS system 300, 400, for example. Reconfiguration information, a reboot or reset instruction, Wi-Fi credentials, etc., can be provided in response to the event, for example.

If the response is determined to be a reconfiguration of the affected device 502-506, then, at block 1206, reconfiguration information is provided for output at block 1020 to the device 502-506. For example, receiver parameters can be adjusted to operate on a different frequency, with a different time interval, looking for another beacon, at a different power level, with a heartbeat adjustment, etc. If the response is determined to be a reset of the affected device 502-506, then, at block 1208, a reset command is sent for output at block 1020 to the device 502-506 to reset the device 502-506 in a default or factory state, etc. If the response is determined to be a reboot, then, at block 1210, a reboot command is sent for output at block 1020 to the affected device 502-506 to reboot or restart the device 502-506. If the response is determined to be to generate a log of the event, then, at block 1212, a log entry is generated to be conveyed to a user, another system, etc., in the output of block 1020. If the response is determined to be maintenance of the affected device 502-506, then, at block 1214, a maintenance request is generated for output at block 1020 to a service center, operator, scheduling system, maintenance professional, etc. If the response is determined to be an alert, then, at block 1216, an alert is generated for output at block 1020 to an operator, other system, service center, log, user interface, etc. For example, an alarm (e.g., an alphanumeric, audible, visual, haptic, and/or other alarm) can be generated as an alert. A charging reminder can be generated as an alert, for example.

At block 1218, if an additional response is to be provided, then control returns to block 1204. Otherwise, control returns to block 1020 to generate an output.

Figure 13:
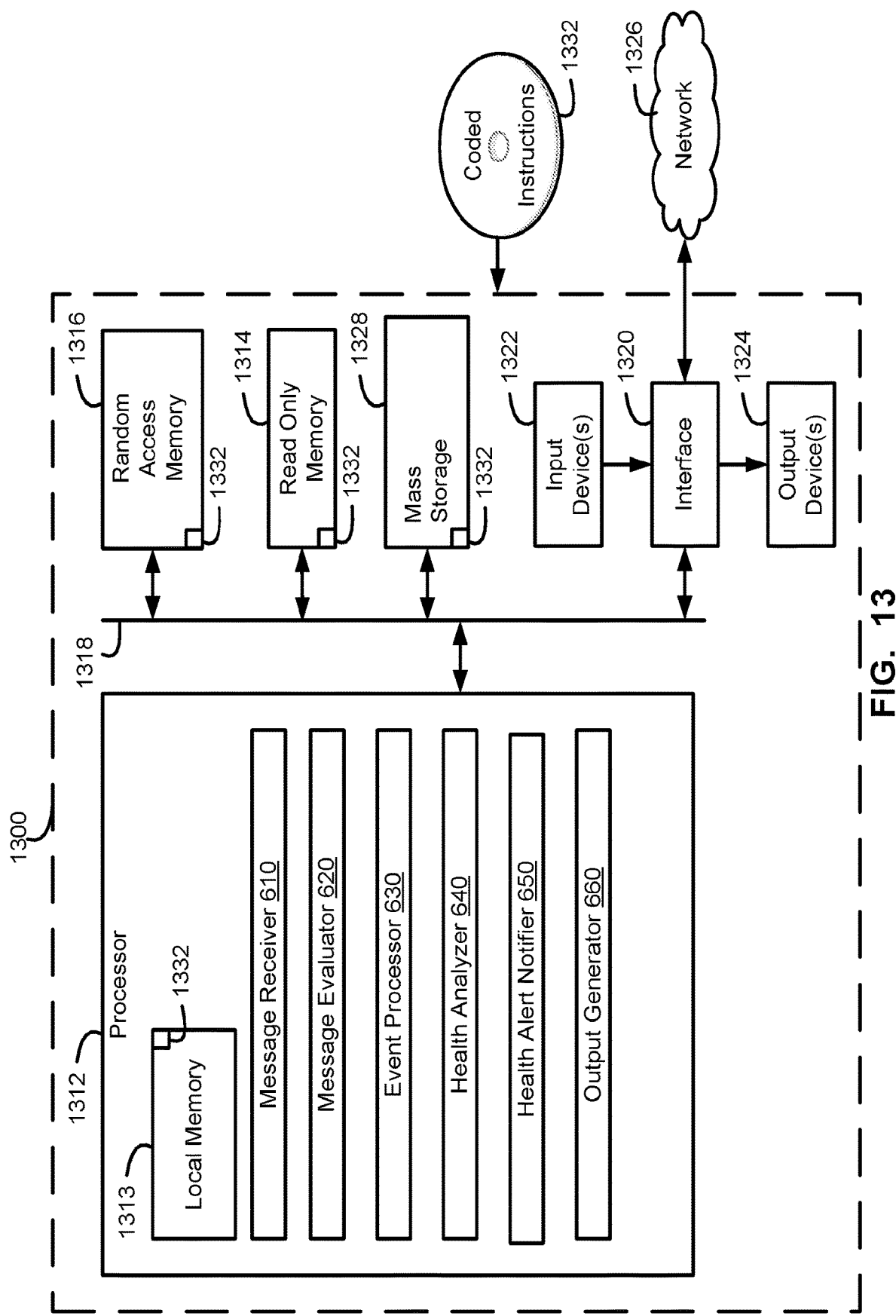
FIG. 13 is a block diagram of an example server structured to execute the example machine-readable instructions of FIGS. 10-12 to implement the example systems of FIGS. 1-9.

FIG. 13 is a block diagram of an example processor platform 1300 capable of executing the instructions of FIGS. 10-12 to implement the example systems and components disclosed and described herein with respect to FIGS. 1-9. The processor platform 1300 can be, for example, a server, a personal computer, or any other type of computing device.

The processor platform 1300 of the illustrated example includes a processor 1312. The processor 1312 of the illustrated example is hardware. For example, the processor 1312 can be implemented by one or more integrated circuits, logic circuits, microprocessors or controllers from any desired family or manufacturer.

The processor 1312 of the illustrated example includes a local memory 1313 (e.g., a cache). The processor 1312 of the illustrated example executes the instructions to implement the example message receiver 610, the example message evaluator 620, the example event processor 630, the example health analyzer 640, the example health alert notifier 650, the example output generator 660, and/or, more generally, the example health processor of FIGS. 3-6. The processor 1312 of the illustrated example is in communication with a main memory including a volatile memory 1314 and a non-volatile memory 1316 via a bus 1318. The volatile memory 1314 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1316 may be implemented by flash memory and/or any other desired type of memory device. Access to the main memory 1314, 1316 is controlled by a memory controller.

The processor platform 1300 of the illustrated example also includes an interface circuit 1320. The interface circuit 1320 may be implemented by any type of interface standard, such as an Ethernet interface, a universal serial bus (USB), and/or a PCI express interface.

In the illustrated example, one or more input devices 1322 are connected to the interface circuit 1320. The input device(s) 1322 permit(s) a user to enter data and commands into the processor 1312. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1324 are also connected to the interface circuit 1320 of the illustrated example. The output devices 1324 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1320 of the illustrated example, thus, typically includes a graphics driver card, a graphics driver chip or a graphics driver processor.

The interface circuit 1320 of the illustrated example also includes a communication device such as a transmitter, a receiver, a transceiver, a modem and/or network interface card to facilitate exchange of data with external machines (e.g., computing devices of any kind) via a network 1326 (e.g., an Ethernet connection, a digital subscriber line (DSL), a telephone line, coaxial cable, a cellular telephone system, etc.).

The processor platform 1300 of the illustrated example also includes one or more mass storage devices 1328 for storing software and/or data. Examples of such mass storage devices 1328 include floppy disk drives, hard drive disks, compact disk drives, Blu-ray disk drives, RAID systems, and digital versatile disk (DVD) drives.

The coded instructions 1332 of FIGS. 9-12 may be stored in the mass storage device 1328, in the volatile memory 1314, in the non-volatile memory 1316, and/or on a removable tangible computer readable storage medium such as a CD or DVD.

From the foregoing, it will appreciate that the above disclosed methods, apparatus and articles of manufacture facilitate proximity detection and location tracking of assets in an industrial setting. As described above, example disclosures uniquely eliminate the expensive and difficult-to-maintain infrastructure. An example benefit of the disclosed techniques includes determining location awareness of assets in the industrial setting without constructing a new infrastructure. In some disclosed examples, the location awareness of assets is determined by "crowd-sourcing" probability proximity locations of the assets.

While prior RTLS systems and associated devices did not have an ability to provide health status information and communicate between a processor and device(s) to update configuration, restart/reset, alert, and/or otherwise respond to a health event, certain examples provide receivers, beacons, badges, and/or other RTLS devices with electronic circuitry and programming to store, communicate, and respond to health status events. Certain examples provide a health processor, embedded in an edge device and/or implemented in a cloud, that processes system health events and communicates with and controls the RTLS devices to address such health events. Thus, certain examples not only provide new technology previously absent from RTLS devices and associated systems but also provide an ecosystem and infrastructure to help ensure improved RTLS uptime, reliability, automated maintenance/configurability/troubleshooting, and accuracy for health asset monitoring, tracking, and management.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. An apparatus comprising:
a real time location system (RTLS) health processor, the RTLS health processor including:
an event processor to process an event included in a message from an RTLS device to identify event information related to the RTLS device, wherein the RTLS device is remote from the RTLS health processor, the event relating to a health of the RTLS device and the event information including an event type and an event detail, wherein the health of the RTLS device comprises a power level of the RTLS device, a connectivity of the RTLS device, a reboot status of the RTLS device, a heartbeat of the RTLS device, or a combination thereof;
a health analyzer to compare the event detail to a prescribed bound for the event type, the event relating to a health of the RTLS device; and
an output generator to, when the event detail is outside the prescribed bound, trigger a response including an instruction to address the event by adjusting a configuration of the RTLS device, wherein the response comprises at least one of an alarm representing a maintenance request, a reboot, or a heartbeat adjustment, and wherein, when the event detail is inside the prescribed bound, the output generator is to log the event.

2. The apparatus of claim 1, wherein the RTLS device includes at least one of a fixed receiver or a mobile receiver to receive a signal from at least one of a fixed beacon, a mobile beacon, or a badge.

3. The apparatus of claim 1, wherein the RTLS device is to communicate with the health processor via an application programming interface.

4. The apparatus of claim 1, wherein the health processor is to be implemented as a cloud-based health processor.

5. The apparatus of claim 1, wherein the apparatus is to be implemented on an edge device communicating with a cloud.

6. The apparatus of claim 1, wherein the apparatus further includes a user interface device to provide a console displaying, for interaction, information regarding the RTLS device and the event.

7. A non-transitory computer-readable storage medium including instructions that, when executed, cause a processor to be configured to implement a real time location system (RTLS) health processor, the RTLS health processor to include:
- an event processor to process an event included in a message from an RTLS device to identify event information related to the RTLS device, wherein the RTLS device is remote from the RTLS health processor, the event relating to a health of the RTLS device and the event information including an event type and an event detail, wherein the health of the RTLS device comprises a power level of the RTLS device, a connectivity of the RTLS device, a reboot status of the RTLS device, a heartbeat of the RTLS device, or a combination thereof;
- a health analyzer to compare the event detail to a prescribed bound for the event type, the event relating to a health of the RTLS device; and
- an output generator to, when the event detail is outside the prescribed bound, trigger a response including an instruction to address the event by adjusting a configuration of the RTLS device, wherein the response comprises at least one of an alarm representing a maintenance request, a heartbeat adjustment, or a reboot, and wherein, when the event detail is inside the prescribed bound, the output generator is to log the event.

8. The computer-readable storage medium of claim 7, wherein the RTLS device includes at least one of a fixed receiver or a mobile receiver to receive a signal from at least one of a fixed beacon, a mobile beacon, or a badge.

9. The computer-readable storage medium of claim 7, wherein the RTLS device is to communicate with the health processor via an application programming interface.

10. The computer-readable storage medium of claim 7, wherein the apparatus further includes a user interface device to provide a console displaying, for interaction, information regarding the RTLS device and the event.

11. A processor-implemented method for a real time location system (RTLS), the method comprising:
processing, using a processor, an event included in a message from an RTLS device to identify event information related to the RTLS device, wherein the RTLS device is remote from the processor, the event relating to a health of the RTLS device and the event information including an event type and an event detail, wherein the health of the RTLS device comprises a power level of the RTLS device, a connectivity of the RTLS device, a reboot status of the RTLS device, a heartbeat of the RTLS device, or a combination thereof;
comparing, using the processor, the event detail to a prescribed bound for the event type, the event relating to a health of the RTLS device; and
when the event detail is outside the prescribed bound, triggering, using the processor, a response including an instruction to address the event by adjusting a configuration of the RTLS device, wherein the response comprises at least one of an alarm representing a maintenance request, a reboot, or a heartbeat adjustment, and wherein, when the event detail is inside the prescribed bound, logging the event.

* * * * *